US012770068B2

(12) United States Patent
Pottinger et al.

(10) Patent No.: US 12,770,068 B2
(45) Date of Patent: Oct. 20, 2026

(54) SYSTEMS FOR END-TO-END OPTIMIZATION OF PRECISION FERMENTATION-PRODUCED ANIMAL PROTEINS IN FOOD APPLICATIONS

(71) Applicant: Clara Foods Co., Daly City, CA (US)

(72) Inventors: A Samuel Pottinger, Daly City, CA (US); Dane Mathias Jacobson, Newton, MA (US); Ranjan Patnaik, Daly City, CA (US); Varsha Gopalakrishnan, Daly City, CA (US); Zachary Friar, Redwood City, CA (US)

(73) Assignee: Clara Foods Co., Daly City, CA (US)

( * ) Notice: Subject to any disclaimer, the term of this patent is extended or adjusted under 35 U.S.C. 154(b) by 515 days.

(21) Appl. No.: 18/513,497

(22) Filed: Nov. 17, 2023

(65) Prior Publication Data

US 2024/0161873 A1 May 16, 2024

Related U.S. Application Data

(63) Continuation of application No. PCT/US2022/030382, filed on May 20, 2022.

(Continued)

(51) Int. Cl.

| | |
|---|---|
| ***G16B 40/00*** | (2019.01) |
| ***C12P 21/00*** | (2006.01) |
| ***C12R 1/645*** | (2006.01) |
| ***G06N 20/00*** | (2019.01) |
| ***G06N 20/20*** | (2019.01) |
| ***G16B 30/00*** | (2019.01) |
| ***G16B 50/30*** | (2019.01) |

(52) U.S. Cl.

CPC ............ *G06N 20/20* (2019.01); *G06N 20/00* (2019.01); *G16B 30/00* (2019.02); *G16B 40/00* (2019.02); *G16B 50/30* (2019.02); *C12P 21/00* (2013.01); *C12R 2001/645* (2021.05)

(58) Field of Classification Search

CPC ........ G16B 40/00; G16B 30/00; G16B 50/30; G06N 20/00; G06N 20/10; G06N 20/20; C12P 21/00; C12R 2001/645

See application file for complete search history.

(56) References Cited

U.S. PATENT DOCUMENTS

2008/0104003 A1 5/2008 Macharia et al.
2009/0117647 A1 5/2009 Buddhi Srinivasa et al.

(Continued)

FOREIGN PATENT DOCUMENTS

WO WO 2020/165043 A1 8/2020

OTHER PUBLICATIONS

PCT International Search Report and Written Opinion, PCT Application No. PCT/US22/30382, Dec. 13, 2022, 22 pages.

*Primary Examiner* — Shane D Woolwine

(74) *Attorney, Agent, or Firm* — Fenwick & West LLP

(57) ABSTRACT

Provided herein are methods for precision fermentation that iteratively build models, collect data broadly, and deliver information to users both directly (via API or user interface) or through third party software. Furthermore, in addition to traditional facades and coordinated operations like sagas, subsystems often require the ad-hoc ability to communicate with each other like to operate on data about the same sample or strain across multiple services.

58 Claims, 25 Drawing Sheets

Related U.S. Application Data

(60) Provisional application No. 63/191,272, filed on May 20, 2021.

(56) References Cited

U.S. PATENT DOCUMENTS

| | | | | |
|---|---|---|---|---|
| 2014/0219538 | A1 | 8/2014 | Guthrie et al. | |
| 2014/0287092 | A1 | 9/2014 | Bluck et al. | |
| 2019/0347564 | A1 * | 11/2019 | Kikuchi .................. | G06N 7/01 |

* cited by examiner

SYSTEMS FOR END-TO-END OPTIMIZATION OF PRECISION FERMENTATION-PRODUCED ANIMAL PROTEINS IN FOOD APPLICATIONS

CROSS REFERENCE

This application is a continuation of International Application No. PCT/US2022/030382, filed May 20, 2022, which claims priority to U.S. Provisional Application No. 63/191,272, filed May 20, 2021, the contents of each of which is hereby incorporated by reference in its entirety herein.

BACKGROUND

Yield optimization has long been used in agricultural fields. Improving the output quantity and quality of fermentation-produced animal proteins, however, requires the precise balance of many more interrelated variables.

SUMMARY

Provided herein is a method, comprising: (a) providing a computing platform comprising a plurality of communicatively coupled microservices comprising one or more discovery services, one or more strain services, one or more manufacturing services, and one or more product services, herein each microservice comprises an application programming interface (API); (b) using said one or more discovery services to determine a protein of interest; (c) using said one or more strain services to design a yeast strain to produce said protein of interest; (d) using said one or more manufacturing services to determine a plurality process parameters to optimize manufacturing of said protein of interest using said yeast strain; and (e) using said one or more product services to determine whether said protein of interest has one or more desired characteristics.

In some embodiments, a microservice of said plurality of microservices comprises data storage. In some embodiments, said data storage comprises a relational database configured to store structured data and a non-relational database configured to store unstructured data. In some embodiments, said non-relational database is blob storage or a data lake. In some embodiments, an API of said microservice abstracts access methods of said data storage. In some embodiments, (b) comprises DNA and/or RNA sequencing. In some embodiments, (b) is performed on a plurality of distributed computing resources. In some embodiments, (b) comprises storing results of said DNA and/or RNA sequencing in a genetic database implemented by said one or more discovery services. In some embodiments, (c) comprises using a machine learning algorithm to design said yeast strain. In some embodiments, using said machine learning algorithm to design said yeast strain comprises generating a plurality of metrics about a plurality of yeast strains and, based at least in part on said plurality of metrics, selecting said yeast strain from among said plurality of yeast strains. In some embodiments, said machine learning algorithm is configured to process structured data and unstructured data. In some embodiments, said unstructured data comprises experiment notes and gel images. In some embodiments, using said machine learning algorithm comprises creating one or more containers to store said structured data and said unstructured data and execute said machine learning algorithm. In some embodiments, said plurality of process parameters comprises one or more upstream fermentation parameters and one or more downstream refinement parameters. In some embodiments, said one or more manufacturing services comprises an upstream service to determine said one or more upstream fermentation parameters and a downstream service to determine said one or more refinement parameters. In some embodiments, (d) comprises using computer vision to digitize batch manufacturing records. In some embodiments, (d) comprises using reinforcement learning. In some embodiments, (e) comprises obtaining and processing data from functional tests and human panels. In some embodiments, said plurality of microservices comprise one or more commercial services, and wherein said method further comprises using said one or more commercial services to generate a demand forecast for said protein of interest. In some embodiments, the method further comprises using said demand forecast to adjust one or more process parameters of said plurality of process parameters. In some embodiments, the method further comprises providing access to said plurality of microservices to a user in a graphical user interface, wherein said system providing said graphical user interface has a façade design pattern. In some embodiments, the method further comprises, subsequent to (c), using one or more algorithms to determine if said protein of interest generated by said yeast strain meets one or more requirements. In some embodiments, said one or more discovery services and said one or more strain services are configured to exchange data on relationships between yeast strains and proteins.

Also provided herein is a method for fermentation process optimization, comprising: determining a plurality of input variables with a set of constraints applied thereto, wherein the set of constraints relate to one or more physical limitations or processes of a fermentation system; providing the plurality of input variables with the set of applied constraints to one or more machine learning models; using the one or more machine learning models in a first mode or a second mode, wherein the first mode comprises using a first model to generate a prediction on a given set of input features, and the second mode comprises using the first model and/or an anchor prediction to generate the prediction on the given set of input features and a second model to generate a drag prediction; and using a machine learning algorithm to perform optimization on the prediction(s) from the first mode or the second mode, to identify a set of conditions that optimizes or predicts one or more end process targets of the fermentation system for one or more strains of interest.

In some embodiments, the one or more physical limitations or processes of the fermentation system comprise at least a container or tank size of the fermentation system, a feed rate, a feed type, or a base media volume. In some embodiments, the one or more physical limitations or processes of the fermentation system comprise one or more constraints on Oxygen Uptake Rate (OUR) or Carbon Dioxide Evolution Rate (CER). In some embodiments, the method further comprises using the identified set of conditions to modify one or more of the following: media, pH, duration of fermentation cycle, temperature, feed rate, filtration for one or more impurities, agitation or stirring rate, oxygen uptake, or carbon dioxide generation. In some embodiments, the one or more end process targets comprise end of fermentation titers. In some embodiments, the set of conditions is used to maximize the end of fermentation titers. In some embodiments, the end of fermentation titers is maximized relative to resource utilization including glucose utilization. In some embodiments, the end of fermentation titers is maximized to be in a range of 15 to 50 mg/ml with an OUR constraint of up to 750 mmol/L/hour. In some embodiments, the first and second models are different. In some embodiments, the first and second models are intended to be used in a complementary manner to each other such that inherent characteristics in decision boundaries in the first and second models are accounted for. In some embodiments, the drag prediction by the second model is used as a datapoint to reduce a prediction error of the primary prediction by the first model. In some embodiments, the first and second models are used as derivative free function approximations of a fermentation process in the fermentation system. In some embodiments, the first model is a decision tree-based model. In some embodiments, the first model comprises an adaptive boosting (AdaBoost) model. In some embodiments, the second model comprises a neural network. In some embodiments, the second model comprises an evolutionary algorithm. In some embodiments, the machine learning algorithm that is used for the optimization is different from at least one of the machine learning models that are used to generate the prediction(s). In some embodiments, the machine learning algorithm comprises a genetic algorithm. In some embodiments, the genetic algorithm comprises a Non-dominated Sorting Genetic Algorithm (NSGA-II). In some embodiments, the machine learning algorithm is configured to perform the optimization by running a plurality of cycles across a plurality of different run configurations. In some embodiments, a stopping criteria of at least 0.001 mg/mL is applied to the plurality of cycles. In some embodiments, the machine learning algorithm performs the optimization based at least on one or more parameters including number of generations, generation size, mutation rate, crossover probability, or parents' portion to determine offspring. In some embodiments, a median difference in titer between a predicted fermentation titer and an actual titer for a sample fermentation run is within 10%. In some embodiments, the first model is used to generate one or more out-of-sample predictions on titers that extend beyond or outside of the one or more physical limitations or processes of the fermentation system. In some embodiments, the one or more machine learning models are configured to automatically adapt for a plurality of different sized fermentation systems. In some embodiments, the one or more machine learning models comprises a third model that is configured to predict OUR or CER as a target variable based on the given set of input features. In some embodiments, the given set of input features comprises a subset of features that are accorded relatively higher feature importance weights. In some embodiments, the subset of features comprise runtime, glucose and methanol feed, growth, induction conditions, or dissolved oxygen (DO) growth. In some embodiments, the one or more machine learning models are trained using a training dataset from a fermentation database. In some embodiments, the training dataset comprises at least 50 different features. In some embodiments, the OUR ranges from about 100 mmol/L/hour to 750 mmol/L/hour. In some embodiments, the CER ranges from about 100 mmol/L/hour to 860 mmol/L/hour. In some embodiments, the training dataset comprises at least 5000 data points. In some embodiments, the one or more machine learning models are evaluated or validated based at least on a mean absolute error score using a hidden test set from the fermentation database.

Another aspect provided herein is a method for fermentation process optimization, comprising: monitoring or tracking one or more actual end process targets of a fermentation system; identifying one or more deviations over time by comparing the one or more actual end process targets to one or more predicted end process targets, wherein the one or more predicted end process targets are predicted using one or more machine learning models that are usable in a first mode or a second mode, wherein the first mode comprises using a first model to generate a prediction on a given set of input features, and the second mode comprises using the first model and/or an anchor prediction to generate the prediction on the given set of input features and a second model to generate a drag prediction; and determining, based at least on the one or more deviations over time, adjustments to be made to one or more process conditions in the fermentation system for optimizing the one or more actual end process targets in one or more subsequent batch runs. In some embodiments, the one or more process conditions comprise media, pH, duration of fermentation cycle, temperature, feed rate, filtration for one or more impurities, agitation or stirring rate, oxygen uptake, or carbon dioxide generation.

In some embodiments, the method further comprises continuously making the adjustments to the one or more process conditions for the one or more subsequent batch runs as the fermentation system is operating. In some embodiments, the adjustments are dynamically made to the one or more process conditions in real-time. In some embodiments, the one or more process conditions comprises a set of upstream process conditions in the fermentation system. In some embodiments, the one or more process conditions comprises a set of downstream process conditions in the fermentation system. In some embodiments, the one or more actual end process targets comprise measured end of fermentation titers, and the one or more predicted end process targets comprise predicted end of fermentation titers that are predicted using the one or more machine learning models. In some embodiments, optimizing the one or more actual end process targets comprise maximizing the measured end of fermentation titers for the one or more subsequent batch runs. In some embodiments, the first and second models are different. In some embodiments, the first and second models are intended to be used in a complementary manner to each other such that inherent characteristics in decision boundaries in the first and second models are accounted for. In some embodiments, the drag prediction by the second model is used as a datapoint to reduce a prediction error of the primary prediction by the first model. In some embodiments, the first and second models are used as derivative free function approximations of a fermentation process in the fermentation system. In some embodiments, the first model is a decision tree-based model. In some embodiments, the first model comprises an adaptive boosting (AdaBoost) model. In some embodiments, the second model comprises a neural network. In some embodiments, the second model comprises an evolutionary algorithm. In some embodiments, the one or more predicted end process targets are optimized by a machine learning algorithm. In some embodiments, the machine learning algorithm that is used for the optimization is different from at least one of the machine learning models that are used to generate the prediction(s). In some embodiments, the machine learning algorithm comprises a genetic algorithm. In some embodiments, the genetic algorithm comprises a Non-dominated Sorting Genetic Algorithm (NSGA-II). In some embodiments, the one or more end process targets relate to cell viability. In some embodiments, the set of conditions is used to maximize the cell viability. In some embodiments, the one or more actual end process targets comprise measured cell viability, and the one or more predicted end process targets comprise predicted cell viability that are predicted using the one or more machine learning models. In some embodiments, optimizing the one or more actual end process targets comprise maximizing the measured cell viability for the one or more subsequent batch runs. In some embodiments, optimizing the one or more actual end process targets comprises making the adjustments to the one or more process conditions, to ensure that a number of cells per volume of media for the one or more subsequent batch runs does not fall below a predefined threshold. In some embodiments, the more actual end process targets comprise an operational cost and/or a cycle time for running the fermentation system.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
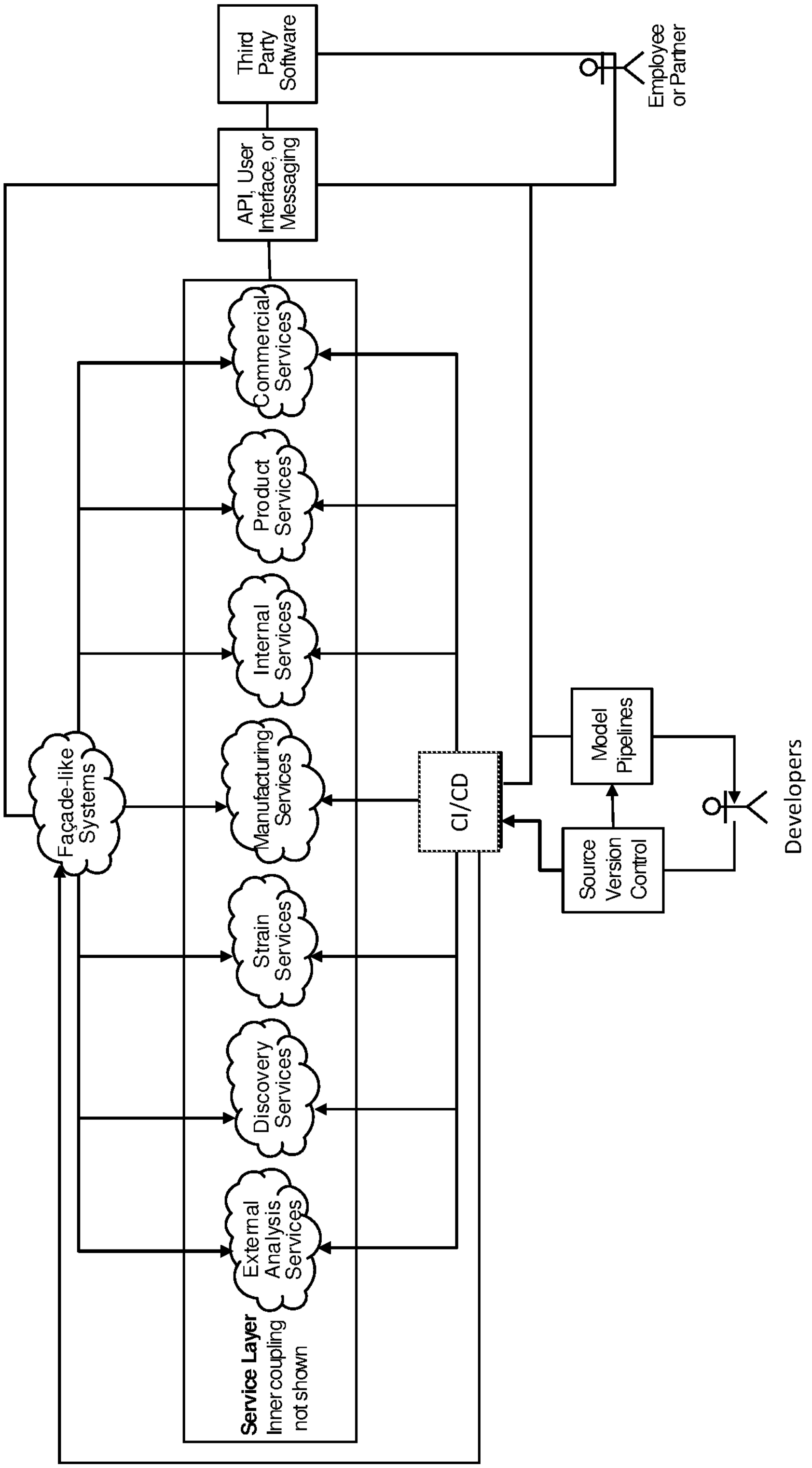
FIG. 1 shows a block diagram of a broad system, per one or more embodiments herein.
Figure 2:
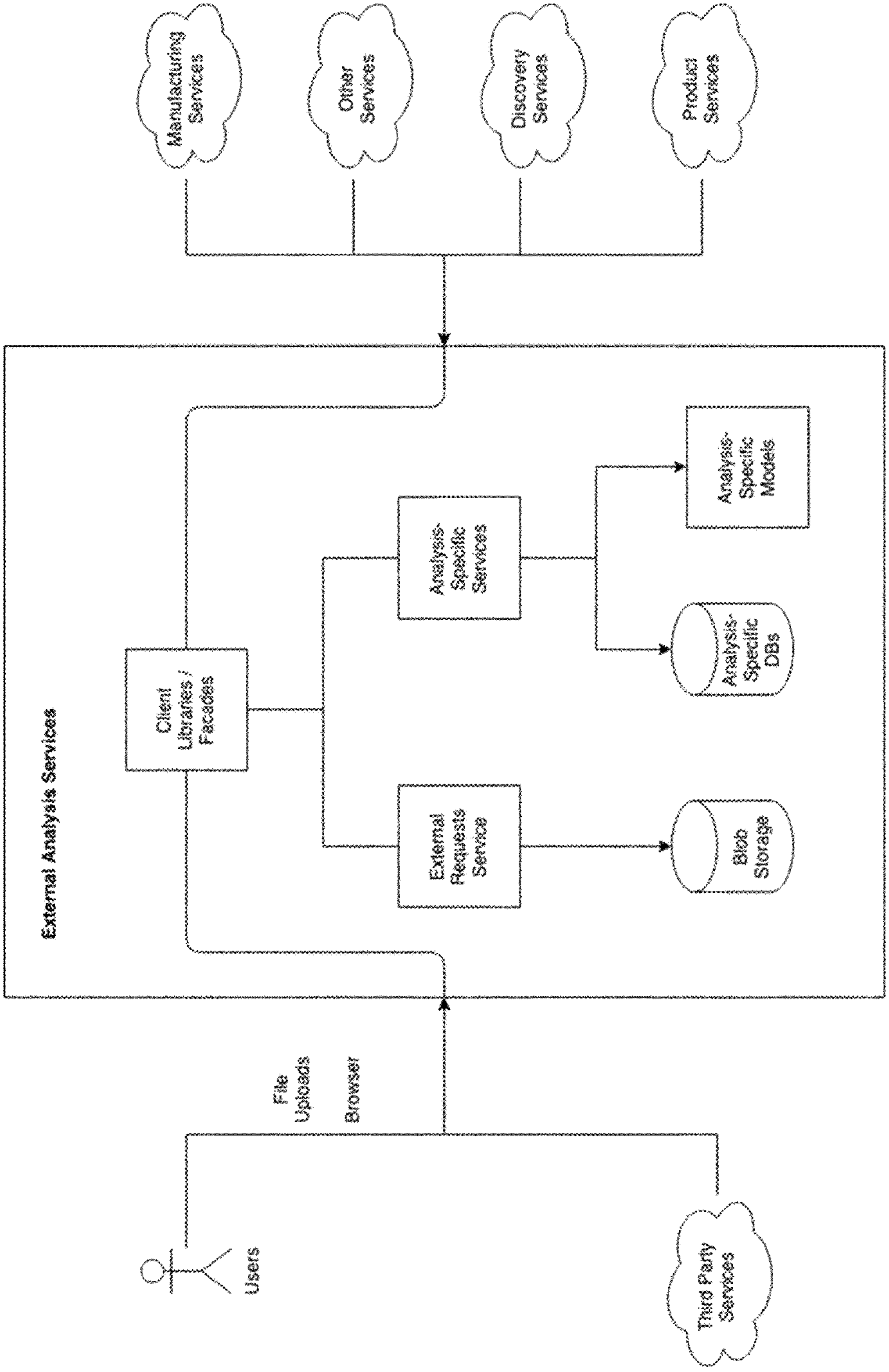
FIG. 2 shows a block diagram of external analysis services, per one or more embodiments herein.

Machine approaches to understanding genetics continue to evolve with, for example, deep learning both in protein design and in understanding the complex mechanisms behind expression. This work extends to new approaches to motif-based modeling. This in mind, multiple approaches in computational strain design explore how machine learning may inform strain modifications and so called "end-to-end" approaches attempt to span intelligence across multiple steps of a development pipeline, enabling more holistic modeling.

Despite this progress, much of the literature's focus on topics like biofuels or therapeutics leave challenges. Considering food specifically, an increase in yields may lead to human perceived decreases in quality where those measures of performance encompass many applications. Furthermore, evaluation of those properties typically requires relatively large amounts of product only possible after some amount of "scale up" in production which itself may require modeling.

Manufacturing

Prior work explores methods for optimizing the parameters of fermentation operations, including the application of machine learning. In some embodiments, the food applications herein present two challenges less explored in the literature. First, like in strain design, modeling in this space must not only consider the "optimizing" metric of yield but also the "satisficing" metric of quality, the latter of which is often defined by difficult to measure attributes like certain taste or human experiences of the product. While the literature does explore machine measurement of these qualities and their prediction, further work may be required in fermentation-produced animal protein specifically. Second, provided herein is a unique pairing of scale with these quality demands. Very few other domains require both the size of production and sensitivity to such a broad array of sensory/functional properties like that required in this space, leaving room for further innovation.

Product and Commercial

While product teams working in food do optimize against directly measurable attributes like gelation and foaming, the gold standard remains "sensory" panels to explore the human experience of a product. Prior work in statistics and artificial intelligence explores methods to better leverage data from these kinds of human panels. Furthermore, prior work explores prediction and interpretation of these results in a food context through many different types of input data. That said, in part due to the novelty of its application in food, the literature remains thin on the use of sensory characteristics in biomanufacturing or strain formulation optimization despite their importance to businesses. Also, consider the myriad of ways in which eggs appear in different food products, each with their own sensory and functional expectations.

Need for New Work

The specific intersection between fermentation, strain design, and the human experience of food creates opportunity for new data science innovation. First, the collection of these disparate types of data into a single system represents a challenge. Second, machine learning for complex response variables like taste requires the coordination of many models and data systems in order to allow for artificial intelligence to optimize with a "full view" into the problem. Therefore, provided herein are methods and systems to model holistically ("end-to-end") for food applications.

System Design

FIG. 1 shows a block diagram of a broad system. As the introduction observes, successful optimization requires a specific composition of components and coordination across disparate datasets.

This system requires the ability to iteratively build models, collect data broadly, and deliver information to users both directly (via API or user interface) or through third party software. Furthermore, in addition to traditional facades and coordinated operations like sagas, subsystems often require the ad-hoc ability to communicate with each other like to operate on data about the same sample or strain across multiple services. Therefore, starting with the composition of and interaction between components, consider the following broad system diagram.

In some embodiments, speaking, REST-based microservices communicate via HTTPS and Avrol. Notably, each system houses very different data. For example, consider that the commercial services work with traditional information about sales, product may house free text descriptions of product quality, and discovery may hold/process very large genomics payloads. Therefore, each system typically maintains its own data storage, abstracting operations via an API. Though this architecture uses HTTPS and Avro, other wire types (e.g. protocol buffers) and messaging mechanisms (e.g. gRPC) also suffice. Some platforms move processes between machines to maintain constant availability as if the system runs continuously.

Third Party Software

The disclosure herein employs different disciplines, each with their own tools. Therefore, most services offer a machine accessible interface, potentially allowing for an ability to run data into systems like Tableau or JMP. This enables implementation cost reduction.

Resident and Ephemeral Computation

In some embodiments, services may run continuously or pseudo-continuously on platform as-a-service offerings like Amazon Elastic Beanstalk, Google App Engine, or Heroku. However, most of these services optimize for tasks which complete in under a minute. That in mind, some operations like the processing of genomics data may run for long periods of time or across multiple machines. In this case, this system may create virtual machines in cloud computing services to process large or long running requests before those machines auto-terminate after uploading their results. In some embodiments, machines hosting "perpetual" tasks (e.g. running a server) as "resident" computation and these temporary machines for a specific task or set of tasks (which then terminate afterwards) as "ephemeral" computation. In practice, this system uses both resident and ephemeral computational approaches across the entire architecture. In some embodiments, ephemeral computation in particular may reduce costs due to reduction of unused machine capacity.

Software Components

Samples are sent to external organizations for analysis like conducting mass spectrometry. Internal services may capture those data for archival and make them available to other internal services. shows a block diagram of external analysis services.

To understand the utility of these API interactions, consider that amino acid analysis results run through a machine learning-based 12 fingerprint model and may determine sample composition to both inform the performance of fermentation and downstream processing as well as explain the results observed in product sensory panels. Therefore, manufacturing services may, for example, request 12 information to run models (like fermentation parameter optimization) and respond to user requests. The automated nature of this diffusion of data allows learning at scale and, in addition to AAA data, may similarly include datasets such as Fourier Transform Infrared (FTIR) spectra or HPLC chromate.

Discovery Services

Figure 3:
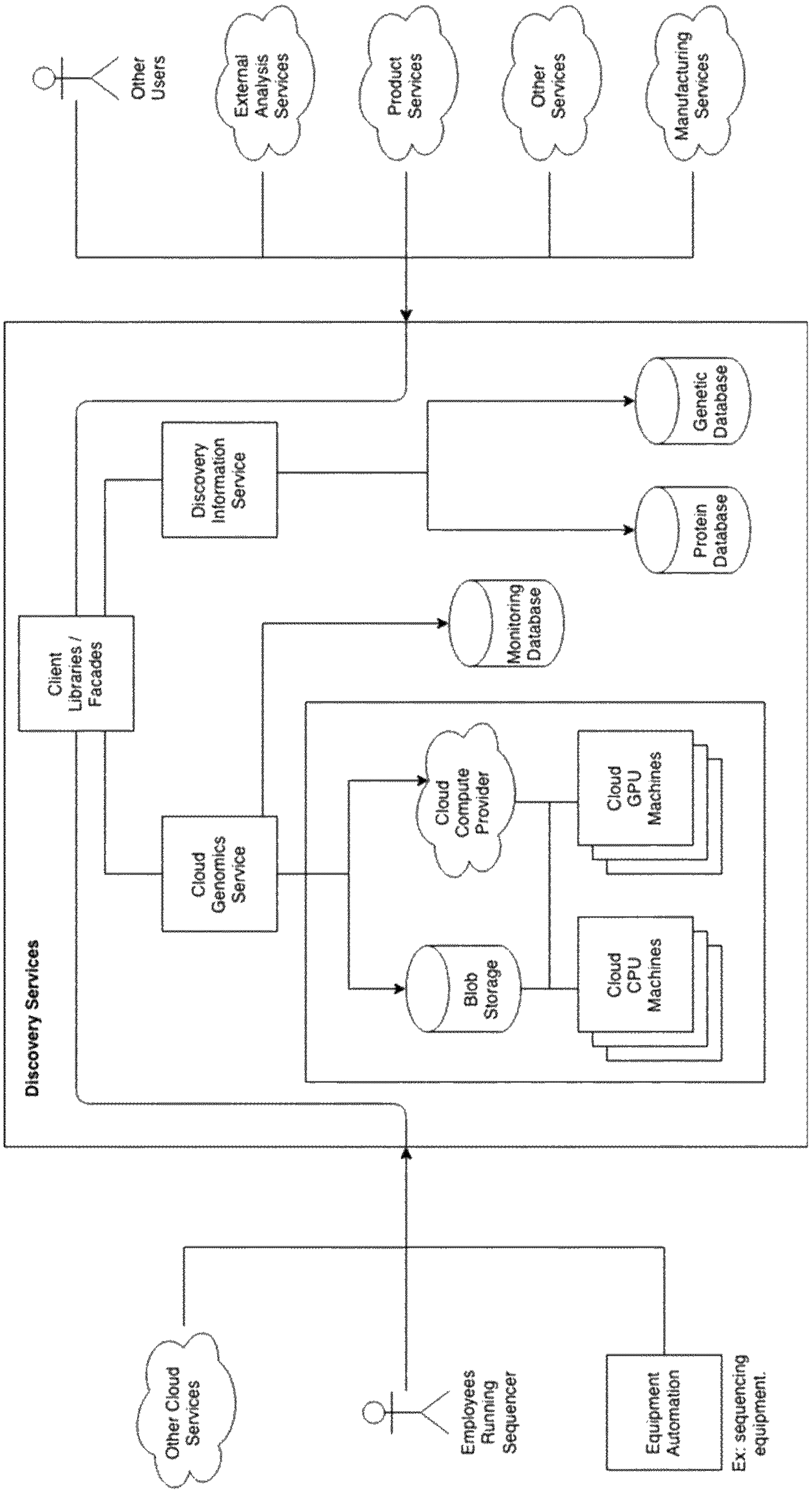
FIG. 3 shows a block diagram of discovery services, per one or more embodiments herein.

Work on designing new strains and determining new proteins of interest requires the manipulation of large unstructured data. For example, sequencing data requires substantial processing (like base calling) before having utility and often results in non-relational output not amenable to most database software. Therefore, the discovery services make extensive use of distributed computing and may use technologies like Spark or Luigi to handle large complex processing pipelines. FIG. 3 shows a block diagram about discovery services.

In practice, these workflows are executed on ephemeral computing due to the requirement of running on large expensive machines. That said, these data connect into information elsewhere in the ecosystem. For example, motif information may join to data within product services about quality or genetic information may link into data from manufacturing and 12 to understand the effect of modifications on product composition.

Strain Services

Figure 4:
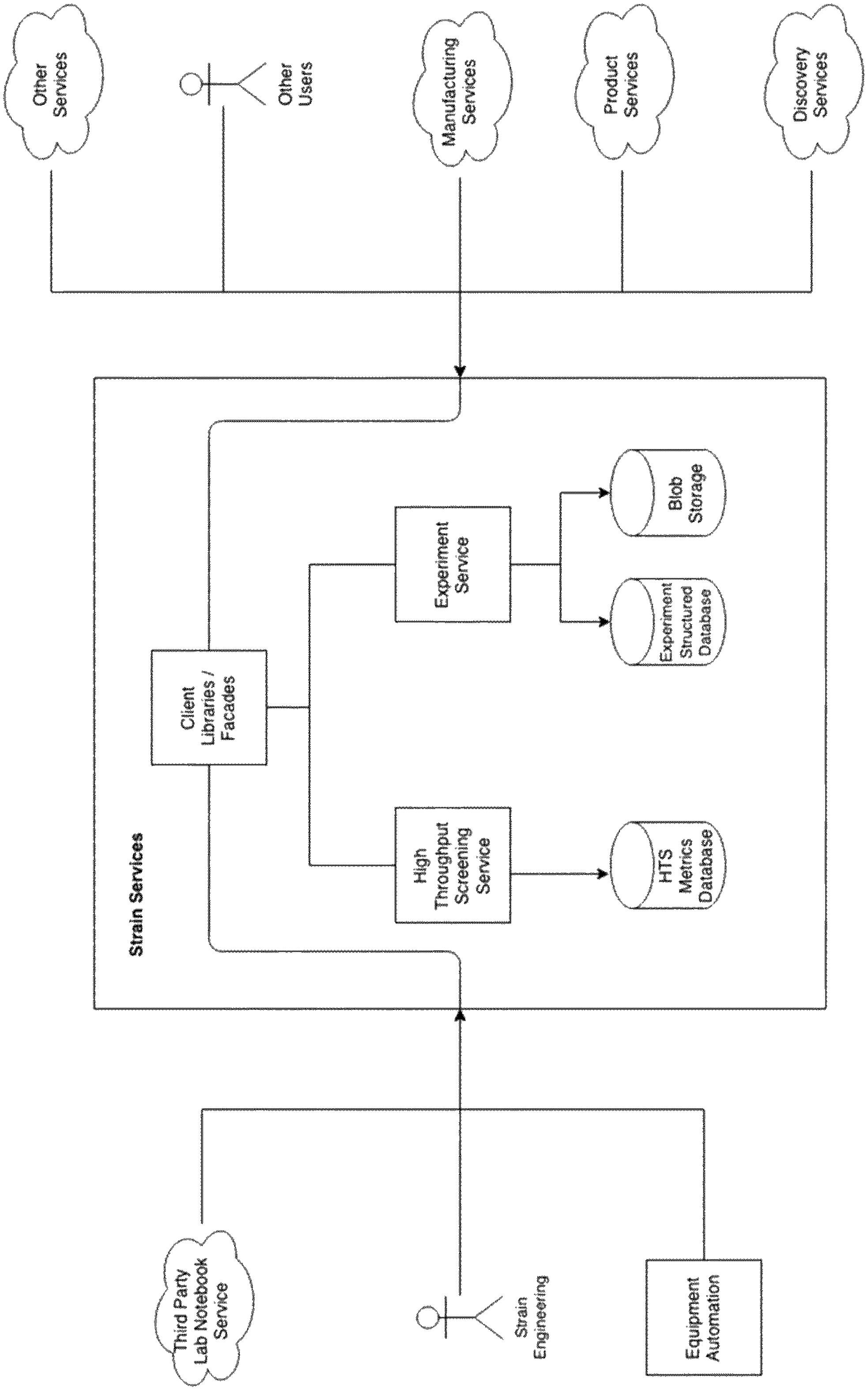
FIG. 4 shows a block diagram of strain services, per one or more embodiments herein.

Strain engineers handle a mixture of structured and unstructured data. High throughput screening systems may emit relational data that allows for the comparison of strains on regularly collected metrics. However, these experiments also produce unstructured data like experiment notes or gel images. These services therefore mix multiple types of storage and create space for the execution of containerized analysis logic in ephemeral computation. Like with other components, data in these services combine with others. These services may also include web-based interfaces for examination of unstructured data in web browsers. For example, HTS data may combine with manufacturing to inform scale up or HTS may inform iterative experimentation captured in discovery services. FIG. 4 shows a block diagram of strain services.

Manufacturing Services

Figure 5:
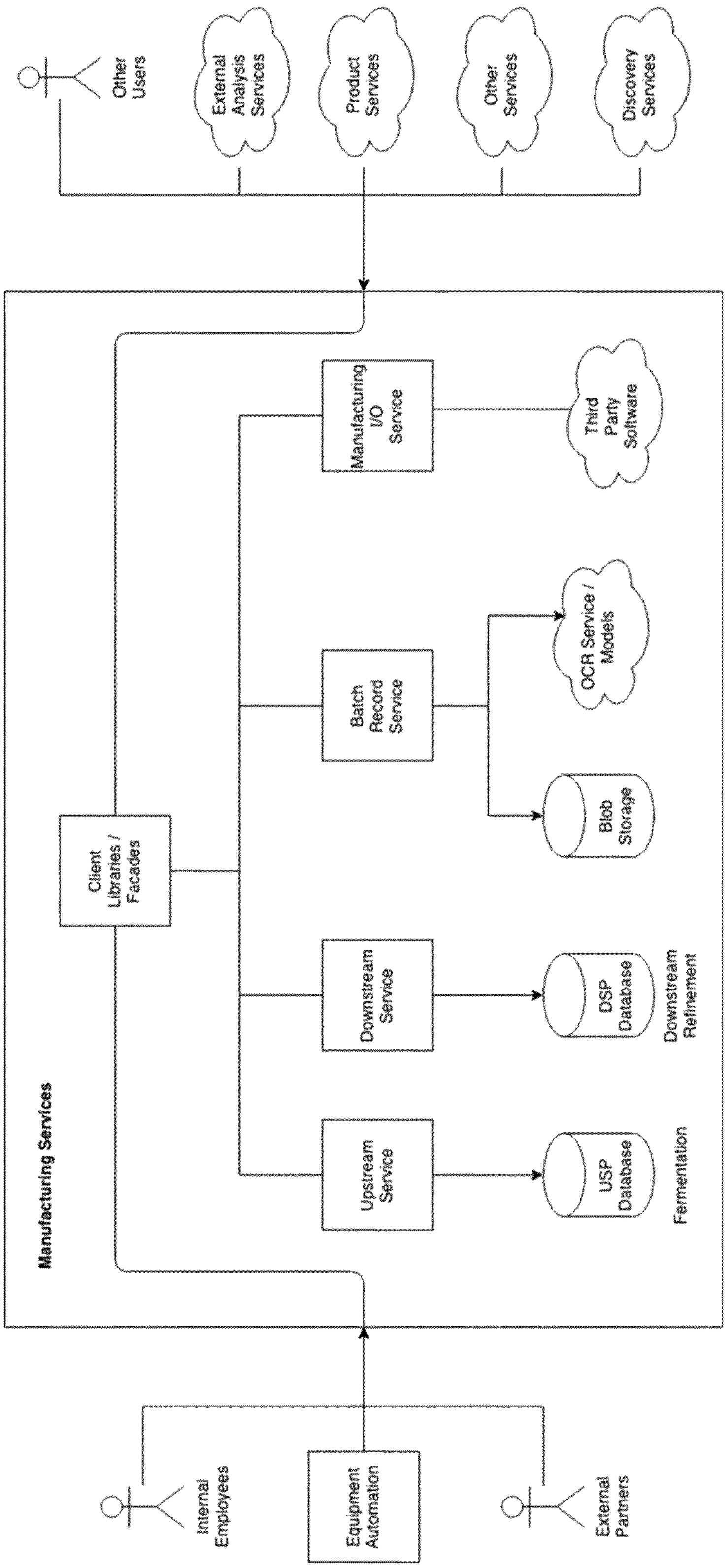
FIG. 5 shows a block diagram of manufacturing services, per one or more embodiments herein.

Manufacturing often generates fairly structured data in large and complex but stable formats. FIG. 5 shows a block diagram of manufacturing services.

However, data arrives from many sources. This in mind, these services may collect information from external APIs or directly from users in different formats. In food specifically, handwriting on paper batch records due to regulatory requirements, necessitates the use of computer vision for digitalization of these data. Regardless, having centralized this information, these manufacturing services then become the primary source of information about a strain's production characteristics. For example, these data may combine with information on quality (product services) or composition (external analysis services) to understand performance dynamics.

Product Services

Figure 6:
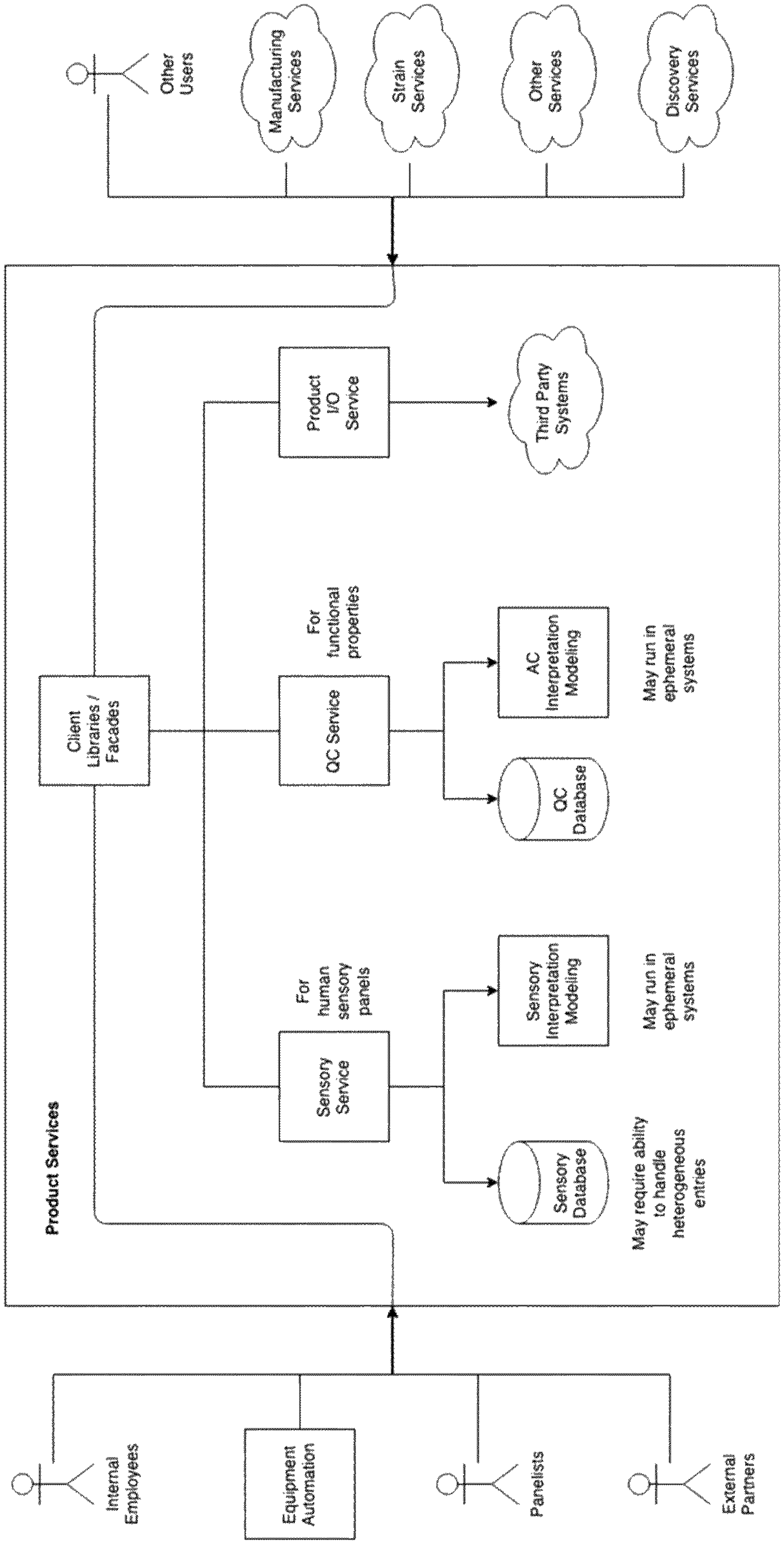
FIG. 6 shows a block diagram of product services, per one or more embodiments herein.

Product services capture both functional tests like pound cake hardness or foaming capacity as well as human panel sensory data whose results are often recorded as Likert-like scales with free text response. Models running in these services enable the proper interpretation of these nuanced data and, as the primary source of information about quality, provide an important perspective to manufacturing, discovery, strain, and other services. FIG. 6 shows a block diagram of product services.

Though typically relational, these data change structure often over time to accommodate different experimental designs so require databases capable of adjusting to dynamic schemas. This may require JSON fields in Postgres or technologies like RethinkDB.

Commercial Services

Figure 7:
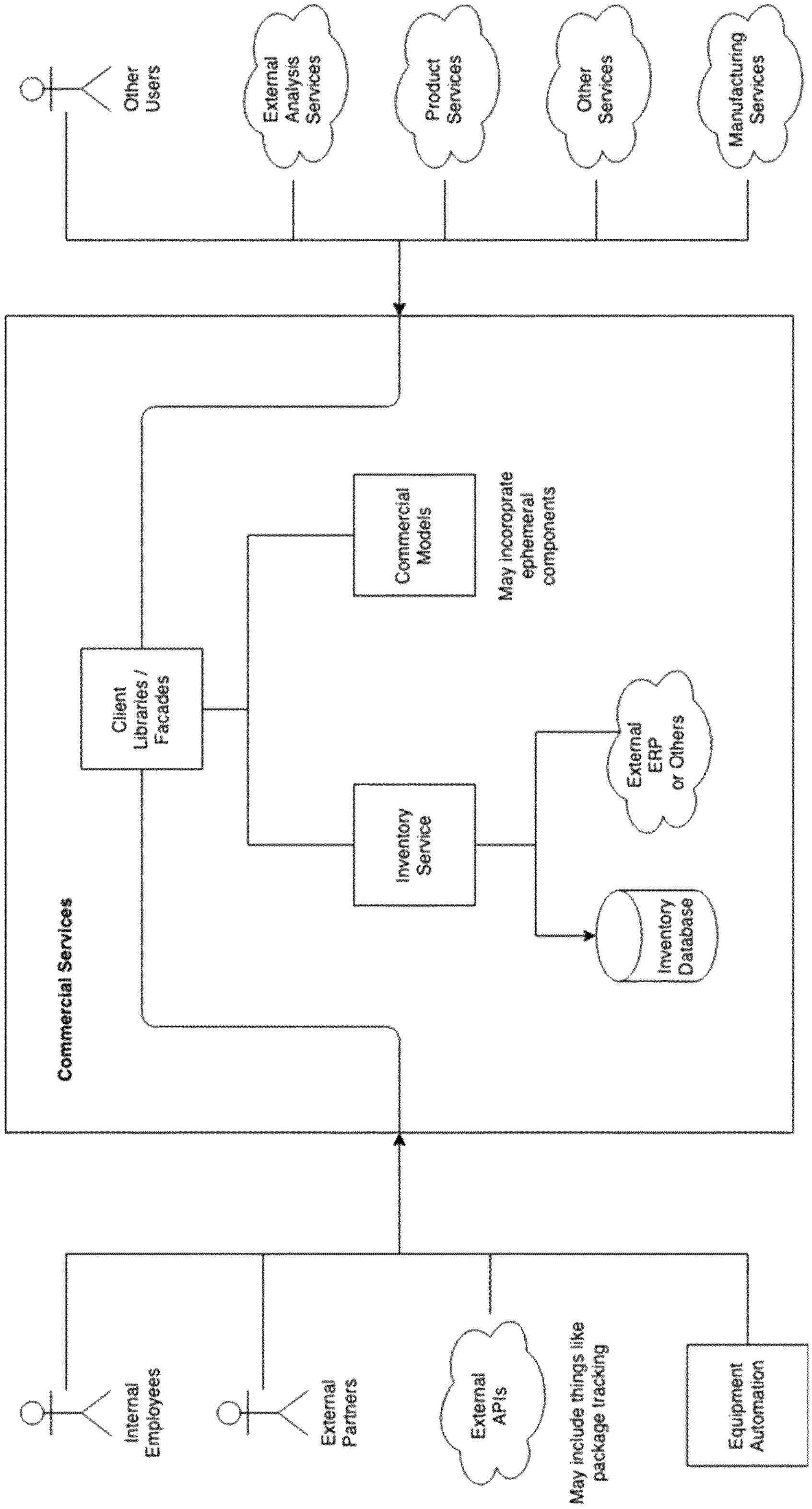
FIG. 7 shows a block diagram of commercial services, per one or more embodiments herein.

In some embodiments, this system may interact with information on sales and customers to understand product demand and performance. Typically these systems simply communicate out to other third party software to collect or report data but may also maintain their own (typically relational) databases. That said, for example, these data may inform fermentation parameter optimization in deciding the number of and timing for production batches. Furthermore, these services may consume information about product availability and QA/QC data. FIG. 7 shows a block diagram of commercial services.

Internal Services

Most services interact with a variety of miscellaneous "internal services" for common functionality like user authentication, sending emails, or recording logs. Like others, these systems maintain their own data storage, typically in the form of relational databases. These services may also help facilitate the mechanics of running models within other services like in authenticating a service account's access to a dataset. In one mode of operation, internal services may house unstructured data (e.g. gel images, high performance liquid chromatography results, or infrared spectra) should they be needed frequently by other services.

Facade-Like Systems

Of course, as a distributed micro-service ecosystem with complex data storage architecture, sagas or facades enable the coordination of data across services with reduced coupling. Typically these systems assist end users (or other services) in execution of complex actions or pull broad datasets from multiple sets of services.

Model Components

To further understand the described software components, this system also briefly explores some of the intelligence within these modules.

Quality Interpretation

Measures of product quality permeate throughout the rest of the described system and is often measured from human panels. While important, these data on difficult topics like mouthfeel often cannot be interpreted without some nuance. Therefore, the described system employs multiple models to ensure high signal when leveraging quality measures in other modeling like in fermentation parameter optimization:

First, the disclosure herein provides mechanisms to set specifications for functional property targets, numerically summarizing the distance between a sample and a standard to provide mathematically founded thresholds for determining if a product meets requirements both on individual properties and in whole.

This system may use z-score normalization and SSRR. Early investigation suggests that these approaches may allow higher level models as a "cleaner" signal such that they may require less data to train through reduced dimensionality.

In short, the architecture's forwarding of quality measures derived through modeling may improve performance across the rest of the system.

Amino Acid Fingerprint

Like interpretation of product quality, modeling of sample composition informs many other models from fermentation parameter optimization to explaining observed changes in sensory qualities. To this end, the fingerprint model (and others like it operating on HPLC/IR) enable insight into samples that give other modeling the signal needed for their predictions and recommendations. Therefore, alongside quality metrics, this modeling enables other data science outcomes elsewhere in the ecosystem. One of skill in the art would recognize that other forms of composition modeling may serve a similar purpose.

Discovery Engine

Figure 8:
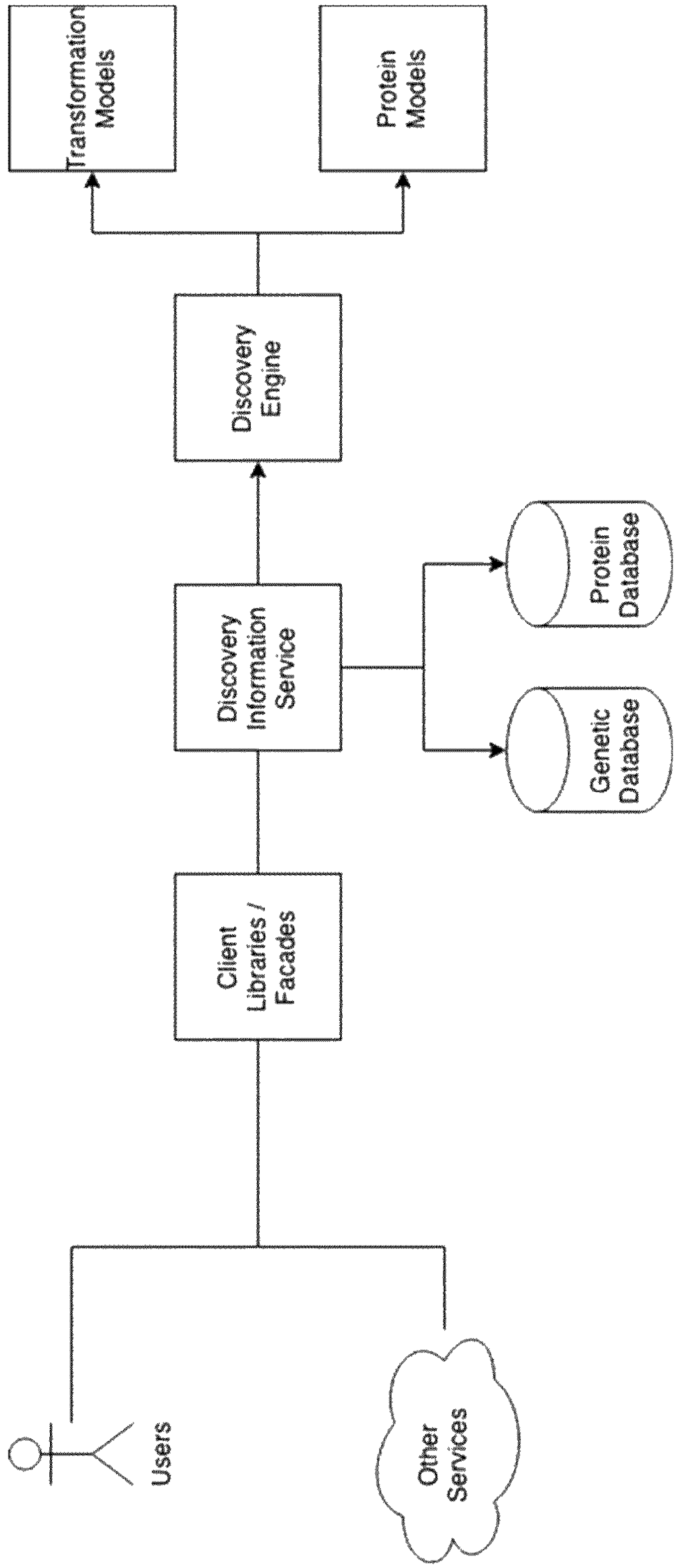
FIG. 8 shows a block diagram of the discovery engine, per one or more embodiments herein.

The disclosed strain and discovery services both create and require data on relationships between strains or proteins (like through phylogenetic or motif-based measures). Paired with information on operational optimization and quality, modeling in this space may help inform finding new proteins of interest or new strain transformations. FIG. 8 shows a block diagram of the discovery engine.

Indeed, this "engine" enabled by the specific interaction between models and components in this architecture may uniquely allow the methods and systems herein to work from functionality backwards to protein/strain, reducing the amount of manual experimentation required. Machine learning in this area remains an active area of internal research.

Batch Record Digitization Services

Figure 9:
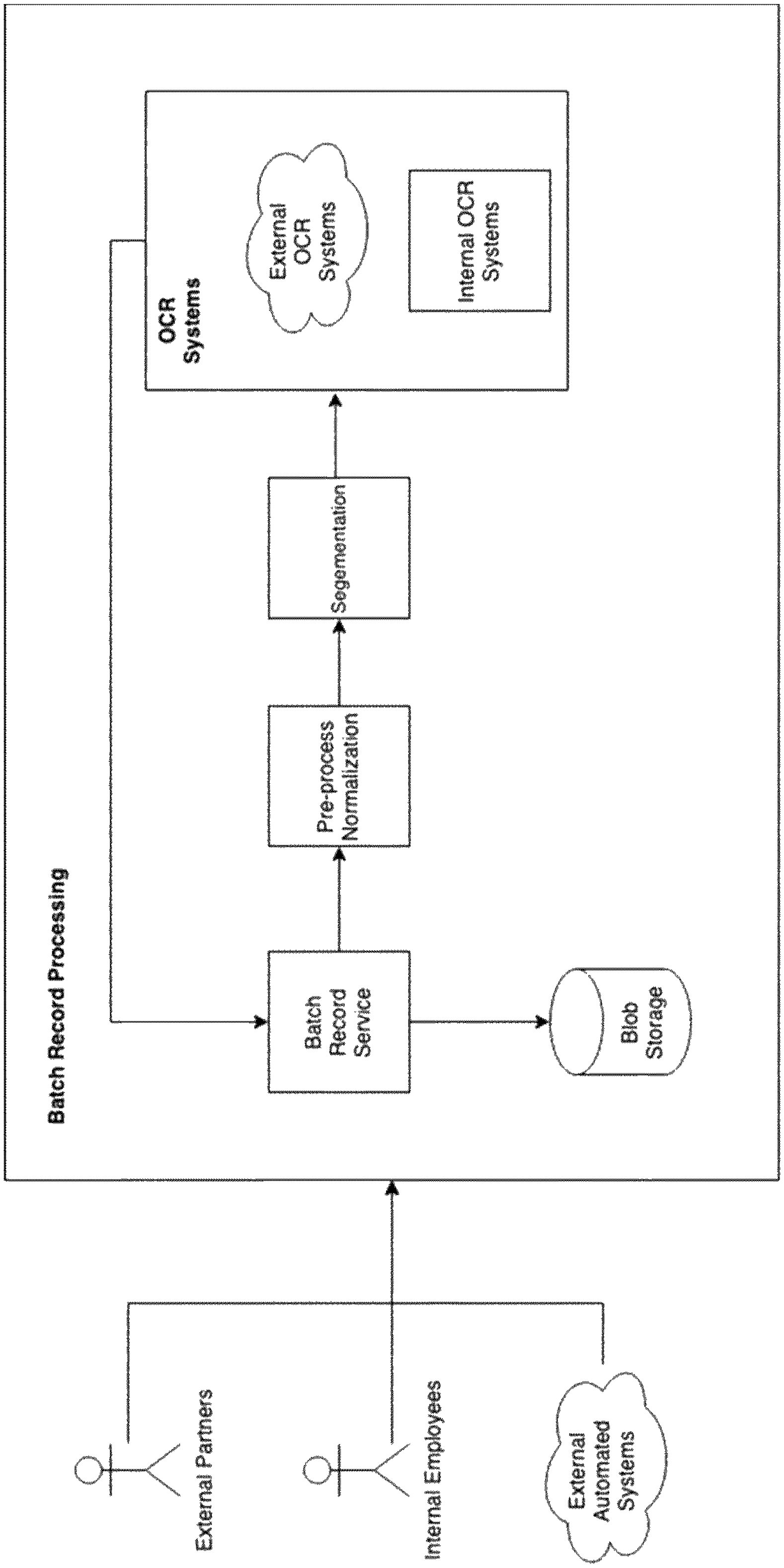
FIG. 9 shows a block diagram of digitalization of batch records, per one or more embodiments herein.

Various modeling like fermentation parameter optimization requires an understanding of the conditions and procedures in which products are produced. However, these records often exist on paper with handwritten notes inside of forms called "batch manufacturing" records ("BMRs"). FIG. 9 shows a block diagram of digitalization of batch records.

Therefore, computer vision models in segmentation and optical character recognition may allow those data to participate in other machine learning efforts at scale, as well as various other kinds of analysis within the described architecture. Without this digitization capability integrated into this larger system, other machine learning efforts may become intractable due to limited sample size.

Operational and Environment Optimization

Parameters and practices from media and environmental conditions to human behaviors influence the performance of a strain and the quality of the final product. Modeling specific to fermentation and downstream operations for food may take inputs from various services and other models to enable the optimization of operations and set points. Of course, such modeling depends on the entire ecosystem of software and modeling. For example, these efforts may require modeling on how scale itself influences strain behavior and quality measures produced elsewhere in the disclosed architecture.

Coordinating Intelligence

Figure 10:
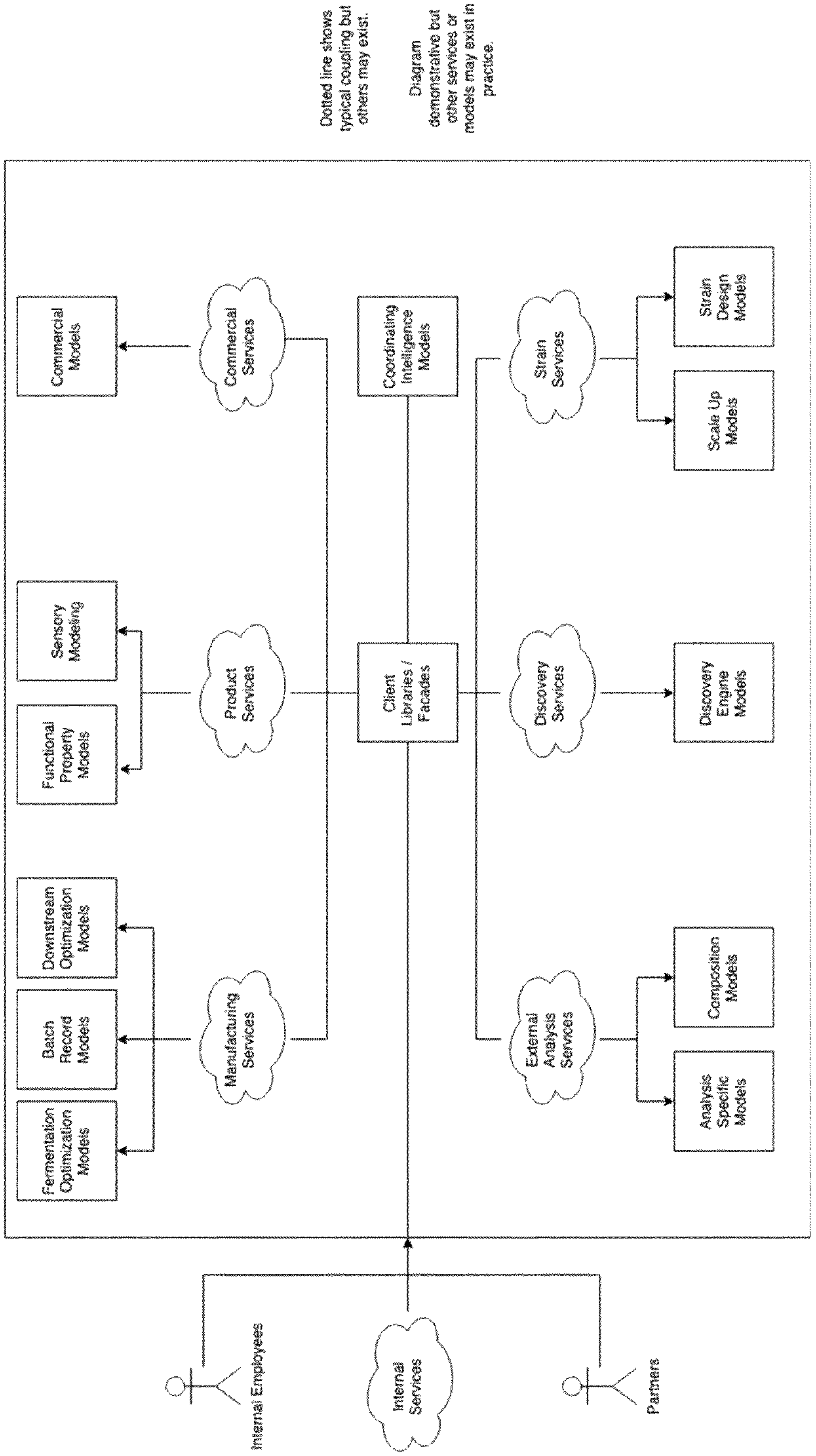
FIG. 10 shows a block diagram of model composition and coordinating intelligence, per one or more embodiments herein.

Many components in this system often focus on individual aspects of operations. However, this architecture suggests that the combination of many of these narrower models' outputs could allow broad system-wide modeling like through reinforcement learning. This "coordinating intelligence" may simultaneously manipulate multiple components of the pipeline such as strain genetics and (scale specific) fermentation parameters. Such modeling may prove intractable without the complex interactions like those enabled by the disclosed design which facilitate communication between components working to create a unified "signal rich" picture of the available data. For example, training on raw 12 data or individual sensory panel responses introduces incredibly large dimensionality into modeling, driving data requirements into likely un-achievable levels. Therefore, the disclosed architecture serves as to satisfy important prerequisites to high level cross-pipeline modeling. FIG. 10 shows a block diagram of model composition and coordinating intelligence. In some embodiments, the coordinating intelligence may also include data visualizations for multiple different types of data used by this modeling.

Egg Proteins

To further explore the disclosed architecture, consider how this system responds to egg proteins specifically, interacts with the product pipeline, and may evolve in the future.

As briefly discussed, eggs present an interesting challenge and opportunity. First, due to egg's versatility, evaluation of egg replacement products requires understanding of both functional properties and sensory characteristics in many different applications and preparation methods. "Leaking" this complexity across the entire system could both increase data requirements and engineering complexity due to higher dimensionality. Therefore, this system's model-based metrics sharpen and summarize (also provide an "encapsulation" from an engineering perspective) the signal from these data so that most other models and systems only work with a "concise" view into this complexity. That said, some models may still choose to work with the full raw input for quality attributes such as sensory and functional tests depending on the amount of nuance required. Second, though less familiar to consumers, protein from other species may prove useful to discovery engine architectures that not only considers proteins from chicken but may incorporate non-production third party or R&D data to recommend other proteins of interest as well.

Finding New Proteins of Interest or Novel Functionalities

Information about protein structure as well as phylogenetic information housed within this system both together may uniquely enable modeling to aid in not just in designing transformations but the identification of new proteins of interest and novel functionality. For example, this system may catalogue information about experiments with new proteins or attempt to infer possible properties of untested proteins to direct experimentation, reducing costs through a more prioritized approach to discovery and enabling product differentiation. However, the utility of these data depend on models' ability to associate this information with other sources such as manufacturing services to understand production dynamics or product services to understand those qualities. This architecture enables that coordination.

Relation to Discovery Platform

In some embodiments, this disclosed system may leverage information from a discovery platform. Specifically, the discovery and strain services capture data from transformations/screening. Furthermore, like for other samples, quality, and applications data feed into product services. That in mind, modeling may use this information for many purposes including providing information about possible future transformations, recommending proteins or protein mixtures, informing scale up parameters and/or predicting performance of new strains. Therefore, this system makes these discovery platform data available like any other dataset and incorporates them broadly into artificial intelligence efforts.

In some embodiments, this system operates across multiple scales and physical locations from bench-top to large production batches. Notably, scale (or location) itself may require changing parameters. Therefore, though the same schema and data systems may capture information across multiple scales of production, the system captures metadata like batch size for modeling.

As operations continue to grow, additional specialized datasets may emerge. This could require the addition of new services or coupling between services/components. In general, the disclosed architecture's use of ephemeral and resident compute as well as its ability to blend different kinds of data storage allow its abstractions to continue to operate even under new complexity. For example, purpose-specific services may exist for HPLC and IR data with heavy processing running on ephemeral compute but made available to the rest of the system via an HTTPS microservice with Avro.

Figure 11:
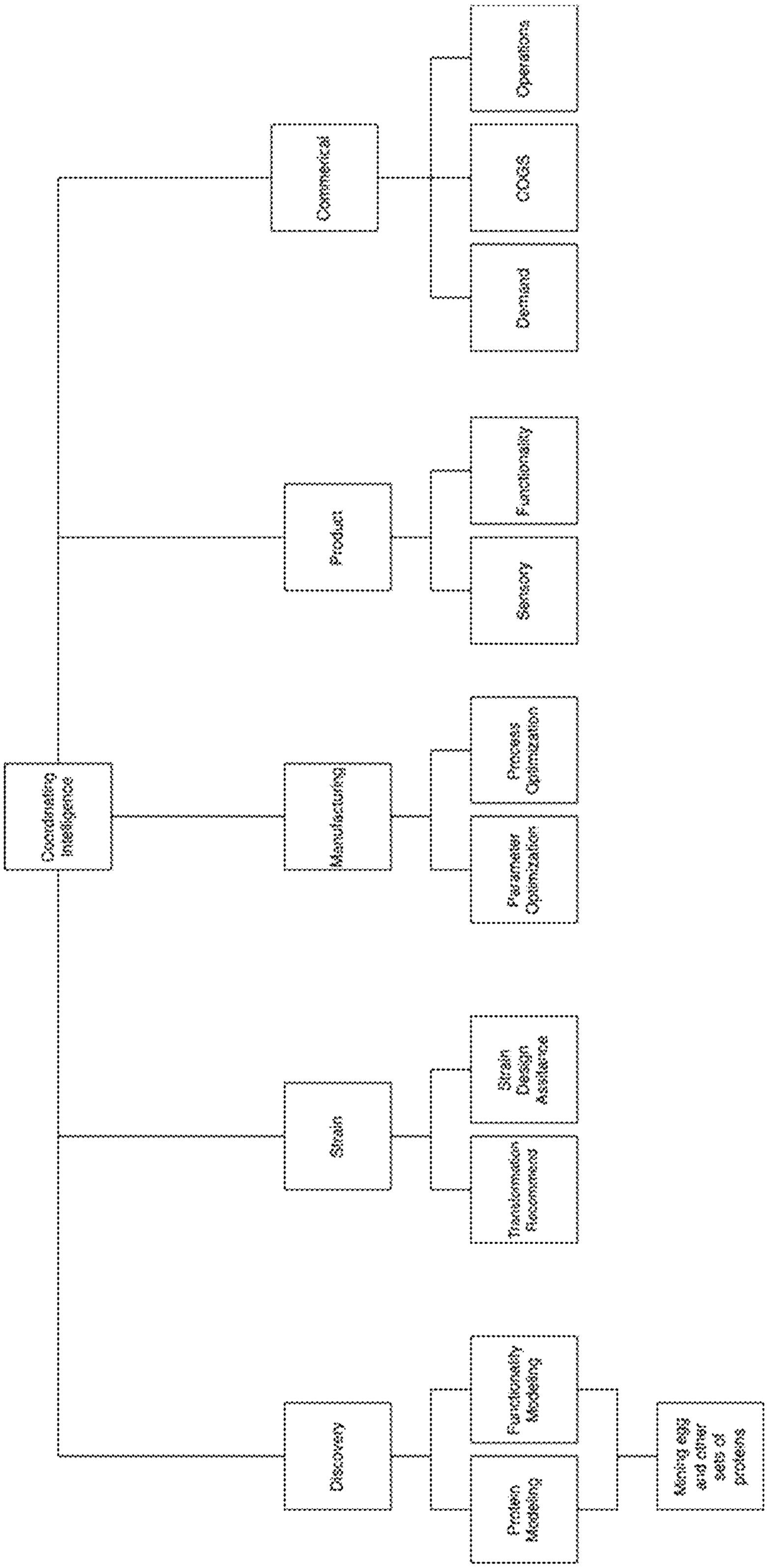
FIG. 11 shows a block diagram of models across different domains, per one or more embodiments herein.

The methods herein requires the collaboration of many different scientific fields and their varied kinds of data. Working from genes to functionality in a human sensory-aware way within the food domain, the machine learning solutions require a broad data warehouse and an infrastructure which may reach across all of these teams. FIG. 11 shows a block diagram of models across different domains.

Therefore, the described system integrates intelligence across all steps the product pipeline and creates structures which allow for the joining together of this highly heterogeneous information. In particular, the disclosure demonstrates how the unification of data from across disciplines may unlock coordinating intelligence not otherwise possible. Furthermore, this study shows how the combination of models may improve data requirements for machine learning given the complex domain-specific information required. While the disclosure is provided towards the manufacture of highly complex food products like egg white substance, these approaches may perform well for other fermentation derived food proteins. The presented microservices architecture weaves machine learning and other forms of modeling into a comprehensive software ecosystem that helps address the complexity of fermentation and egg proteins.

This architecture enables the "end-to-end" coordination of intelligence and software services across a domain-specific digital system aiding precision fermentation produced animal protein. Ranging from protein/functionality identification and genetics to manufacturing and human sensory, this system allows various models to collaborate through highly heterogeneous datasets in order to achieve holistic optimization (quality, volume, COGS) across the many teams and disciplines involved in operations.

Specifically, the presented microservices system weaves machine learning and other forms of modeling into a comprehensive software ecosystem that helps address the complexity of fermentation and egg proteins. Unlike having individual systems for each part of an operation, this architecture allows for the coordinated optimization of quality, quantity, and price by joining together data and models from different scientific disciplines. This requires specific software architectural decisions that blend various kinds of data storage and computation specific to the tasks within this ecosystem. Furthermore, this design describes how modeling operations adjust to these structural decisions. That said, though HTTPS and Avro based microservices are used with tools like Luigi, the same document describes how other embodiments may make different choices in specific technologies.

In one aspect, provided herein is a method comprising: (a) providing a computing platform comprising a plurality of communicatively coupled microservices comprising one or more discovery services, one or more strain services, one or more manufacturing services, and one or more product services, wherein each microservice comprises an application programming interface (API); (b) using said one or more discovery services to determine a protein of interest; (c) using said one or more strain services to design a yeast strain to produce said protein of interest; (d) using said one or more manufacturing services to determine a plurality process parameters to optimize manufacturing of said protein of interest using said yeast strain; and (e) using said one or more product services to determine whether said protein of interest has one or more desired characteristics.

In some embodiments, microservice of said plurality of microservices comprises data storage. In some embodiments, said data storage comprises a relational database configured to store structured data and a non-relational database configured to store unstructured data. In some embodiments, said non-relational database is blob storage or a data lake. In some embodiments, an API of said microservice abstracts access methods of said data storage. In some embodiments, (b) comprises DNA and/or RNA sequencing. In some embodiments, (b) is performed on a plurality of distributed computing resources. In some embodiments, (b) comprises storing results of said DNA and/or RNA sequencing in a genetic database implemented by said one or more discovery services. In some embodiments, (c) comprises using a machine learning algorithm to design said yeast strain. In some embodiments, using said machine learning algorithm to design said yeast strain comprises generating a plurality of metrics about a plurality of yeast strains and, based at least in part on said plurality of metrics, selecting said yeast strain from among said plurality of yeast strains. In some embodiments, said machine learning algorithm is configured to process structured data and unstructured data. In some embodiments, said unstructured data comprises experiment notes and gel images. In some embodiments, using said machine learning algorithm comprises creating one or more containers to store said structured data and said unstructured data and execute said machine learning algorithm. In some embodiments, said plurality of process parameters comprises one or more upstream fermentation parameters and one or more downstream refinement parameters. In some embodiments, said one or more manufacturing services comprises an upstream service to determine said one or more upstream fermentation parameters and a downstream service to determine said one or more refinement parameters. In some embodiments, (d) comprises using computer vision to digitize batch manufacturing records. In some embodiments, (d) comprises using reinforcement learning. In some embodiments, (e) comprises obtaining and processing data from functional tests and human panels. In some embodiments, said plurality of microservices comprise one or more commercial services, and wherein said method further comprises using said one or more commercial services to generate a demand forecast for said protein of interest. In some embodiments, said method further comprises using said demand forecast to adjust one or more process parameters of said plurality of process parameters. In some embodiments, said method further comprises providing access to said plurality of microservices to a user in a graphical user interface, wherein said system providing said graphical user interface has a façade design pattern. In some embodiments, said method further comprises, subsequent to (c), using one or more algorithms to determine if said protein of interest generated by said yeast strain meets one or more requirements. In some embodiments, said one or more discovery services and said one or more strain services are configured to exchange data on relationships between yeast strains and proteins.

Fermentation Parameter Optimization

Provided herein are methods and system comprising a model for determining optimal fermentation conditions to maximize a fermentation titer. In some embodiments, the models are given input parameters (e.g. container size, feed strategy), wherein individual constraints on variables are determined from experimentation or physical limitations.

Figure 14A:
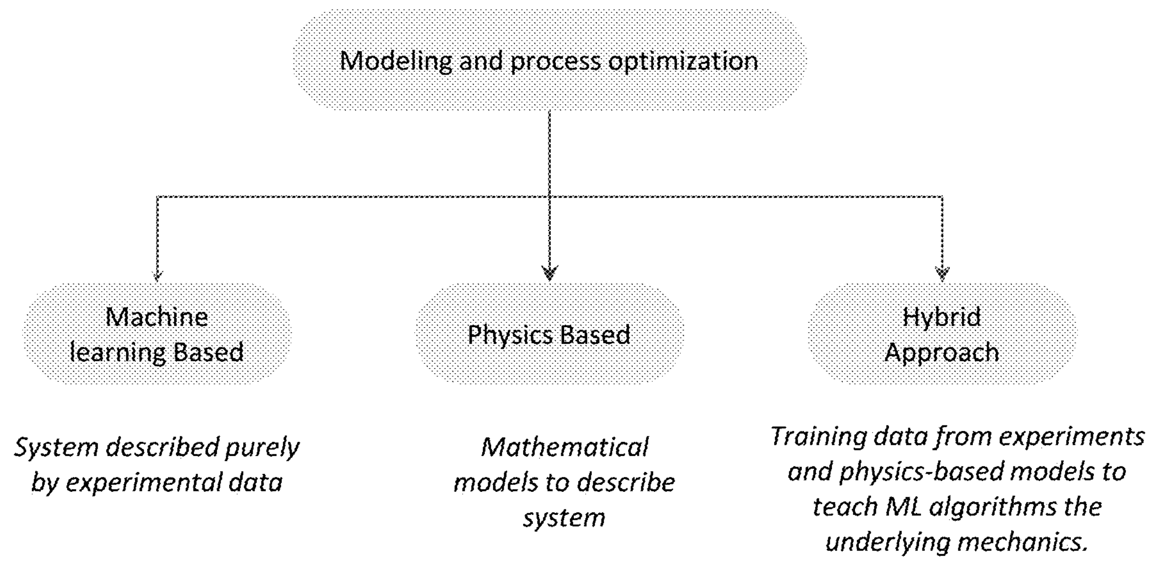
FIG. 14A shows a block diagram of exemplary components for modeling and process optimization, per one or more embodiments herein.

FIG. 14A shows a block diagram of exemplary components for modeling and process optimization. While some models are kinetic or physics-based, that are derived empirically using mathematical equations based on a good understanding of the underlying process, such models may be limited to simple processes with low numbers of variables. As such, in some embodiments, the modeling and process optimization herein employs a combination of machine learning, which describes the system with experimental data, physics models, which describes the system with mathematical equations. As such, in some embodiments, the hybrid approach uses both machine learning and physics-based models for improved modeling and optimization efficacy.

As such, provided herein are data-driven machine learning models trained on experimental data which determine functions that map a set of inputs to an output, while capturing information on parameter ranges. Such models are able to map a system based on experimental data, without a predetermined mathematical model to describe the underlying system, by mapping an entire constraint space to maximize an objective function.

In some embodiments, the Adaboost regression machine learning models herein are trained using standardized data from a variety of sources in the form of a unified fermentation database of experimental data. In some embodiments, the database is updated in real-time, enabling an increased frequency of model retraining for more accurate training. In some embodiments, the Adaboost regression machine learning models herein are trained to predict titer outputs.

In some embodiments, titer prediction is more accurate when the feature set comprises phylogenetic information as well as a Markov-like property, wherein a titer at a given timepoint is dependent on titer and runtime hours at the previous timepoint. In some embodiments, the prediction accuracy of the accuracy of Adaboost regression machine learning models herein depends more upon media conditions than scale and POIs (proteins-of-interest). In some embodiments, such scale and POI independence enables flexibility in the use of a single model to make predictions across different scales and POIs. In some embodiments, tree-based models provide improved performance over neural networks to predict titer outputs. In some embodiments, the Adaboost regression machine learning models herein employ alternative metrics that effectively capture both run cost and final yield after DSP as optimization objectives instead of titer.

In some embodiments, parameter optimization is performed herein using Genetic Algorithm techniques, wherein Adaboost models (tree based) and Neural Network models are used as derivative-free 'data-driven' function approximations of a fermentation process. In some embodiments, candidate fermentation conditions are identified by optimizing for the highest end-of-fermentation titers, while placing constraints on the model that represent physical limitations (e.g. container size) of the system. In some embodiments, constraints (e.g. container size, feed strategies) are imposed on each input variable that feeds into the Adaboost and Neural Network machine learning models.

Reinforcement Learning (RL) is a type of machine learning algorithm that enables an agent to learn in an interactive environment through trial and error based on feedback from actions. In some embodiments, reinforcement learning techniques are employed herein to identify optimal fermentation conditions that may maximize end-of-fermentation titers.

In some embodiments, the models herein employ a Genetic Algorithm (GA) for a heuristic search-based optimization technique. GAs are a class of Evolutionary Algorithm (EA), which may be used to solve problems with a large solution space for both constrained and unconstrained variables. In some embodiments, EAs use only mutation to produce the next generation, while GAs use both crossover and mutation for solution reproduction.

In some embodiments, GA. repeatedly modifies a population of individual solutions selected at random, and then uses the existing population to produce the next generation by mutation and crossover. In some embodiments, GA gradually evolves towards a near-optimal solution with each generation. An exemplary GA comprises: selecting an individual or parent solution that contributes to the next generation's population; combining two parent solution to form a next generation child solution; and randomly selecting individual parents to form children at the next generation.

Figure 12:
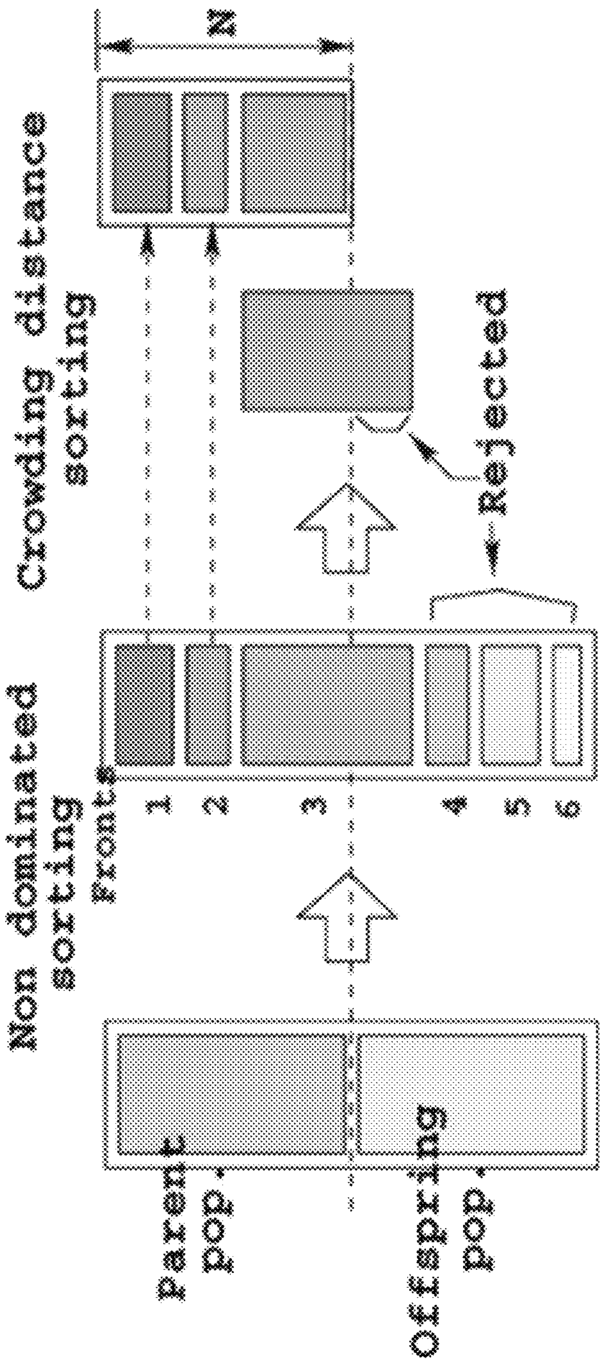
FIG. 12 shows a block diagram of an exemplary NSGA-II algorithm, per one or more embodiments herein.

In some embodiments, NSGA-II (Non-dominated Sorting Genetic Algorithm) is used for optimization herein. In some embodiments, NSGA-II generates offspring based on a specific type of crossover and mutation, selecting the next generation according to a non-dominated-sorting and crowing distance comparison. FIG. 12 shows a block diagram of an exemplary Non-dominated Sorting Genetic Algorithm (NSGA-II) used to solve multi-objective optimization problems. In some embodiments, the NSGA-II requires the following input parameters: number of generations to evolve; population size (number of solution for each generation); crossover probability (chance of a parent solution to pass its characteristic to a child solution); mutation rate (the chance a gene in a parent solution is randomly replaced); and parent proportion (the portion of the solution population comprising the previous generation of solutions). In some embodiments, the NSGA-II algorithm was implemented herein using a framework for multi-objective optimization with a stopping criteria of about 0.001 mg/mL. In some embodiments, a modified EA was implemented to solve the optimization problem to determine solutions at random from the given set of input values for the features that resulted in the highest titers. In some embodiments, a sweep is performed for hyperparameters including: number of generations, generation size, mutation rate, crossover probabilities; parents portion to determine an offspring, or any combination thereof. In some embodiments, the problem is described as:

$$\max(x)[EOF\ \text{Titer}]$$

$$x_i^L \le x_i \le x_i^U$$

$$f_i^L \le f_i \le f_i^U$$

$$\sum(\text{ingredients}) < \text{Capacity}_{tank}$$

In some embodiments, the ingredients comprise glucose, methanol, and a base.

Figure 13:
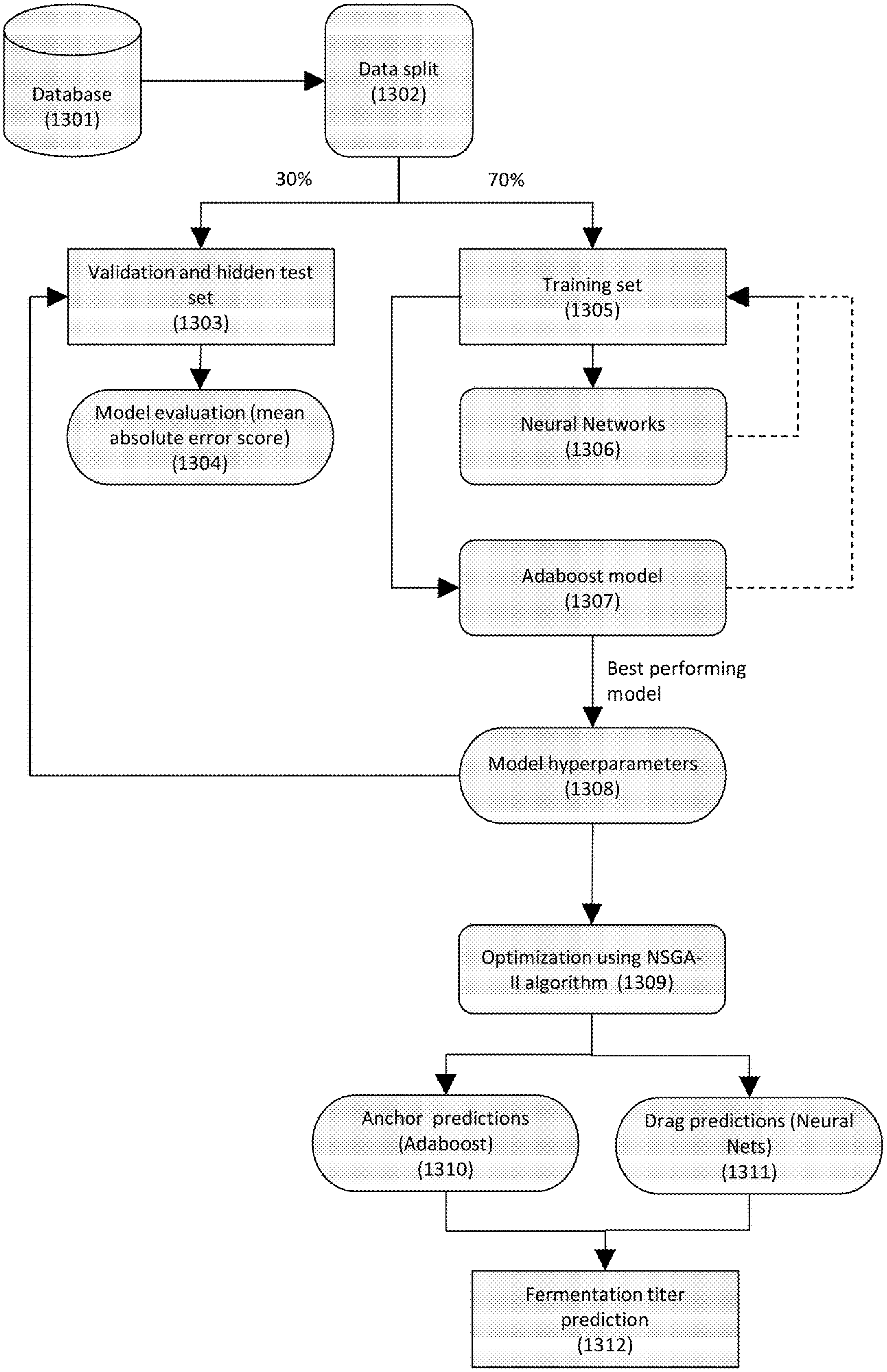
FIG. 13 shows a block diagram of an exemplary fermentation model for titer optimization, per one or more embodiments herein.

FIG. 13 shows a block diagram of an exemplary fermentation model for titer optimization. In some embodiments, this model employs the hyperparameters from the best-performing Adaboost model and the best-performing Neural Network models are used as function approximations in an Anchor-Drag prediction setup to describe a fermentation system. As shown, in some embodiments, 30% of data is split 1302 from a database 1301 to a validation and hidden test set 1303, whereas the remaining 70% of the data is split 1302 to a training set 1305. Further, the training set 1305 is used to train an Adaboost model 1307 and neural networks 1306, which both feedback into the training set 1305. Additionally, as shown, the hyperparameters 1308 of a best performing Adaboost model 1307 is optimized using an NSGA-II algorithm 1309, whereafter Adaboost anchor predictions 1310 and neural network "drag" predictions are used to determine a fermentation titer prediction 1312. In some embodiments, a "drag" neural network model prediction is used as an additional datapoint to reduce prediction error in case there is a tie.

Finally, the hyperparameters 1308 are also added to the validation and hidden test set 1303, wherein the validation and hidden test set 1303 is used to form a Model evaluation comprising a mean absolute error score 1304. In some embodiments, the Adaboost model with the best performing hyperparameters are used to evaluate the validation and hidden test set based on the mean absolute error score. Further, in some embodiments, the best performing Adaboost model is evaluated on the test set using the mean absolute error score. Further, the training set is used to train an Adaboost model and Neural Networks and the performance of the model is evaluated on the validation set. The models are trained continually until the best hyperparameters are determined. Additionally, as shown, the Adaboost model with the best hyperparameters that describe the fermentation system is optimized using an NSGA-II algorithm In some embodiments, as tree based models may exhibit rapidly changing or "unsmooth" decision boundaries, and as neural network models form smooth boundaries, the combination of tree-based and neural networks improves modeling results. In some embodiments, the Adaboost model is used to form a primary or "anchor" prediction for a given set of input conditions. In some embodiments, a margin or leeway of about 10% is used to determine how far the "drag" model may deviate from the anchor prediction. In some embodiments, a "margin" value represents a degree of how close the model is to the anchor prediction.

FIG. 14A shows a block diagram of exemplary components for modeling and process optimization. In some embodiments, the optimization methods and systems herein are "data-driven." In some embodiments, the optimization methods and systems do not require kinetic-based or physics-based system models. In some embodiments, a data-driven model derives knowledge about a system from prior experimental data. In some embodiments, a data-driven model learns functions to map a set of inputs to an output, while capturing parameter ranges.

Figure 14B:
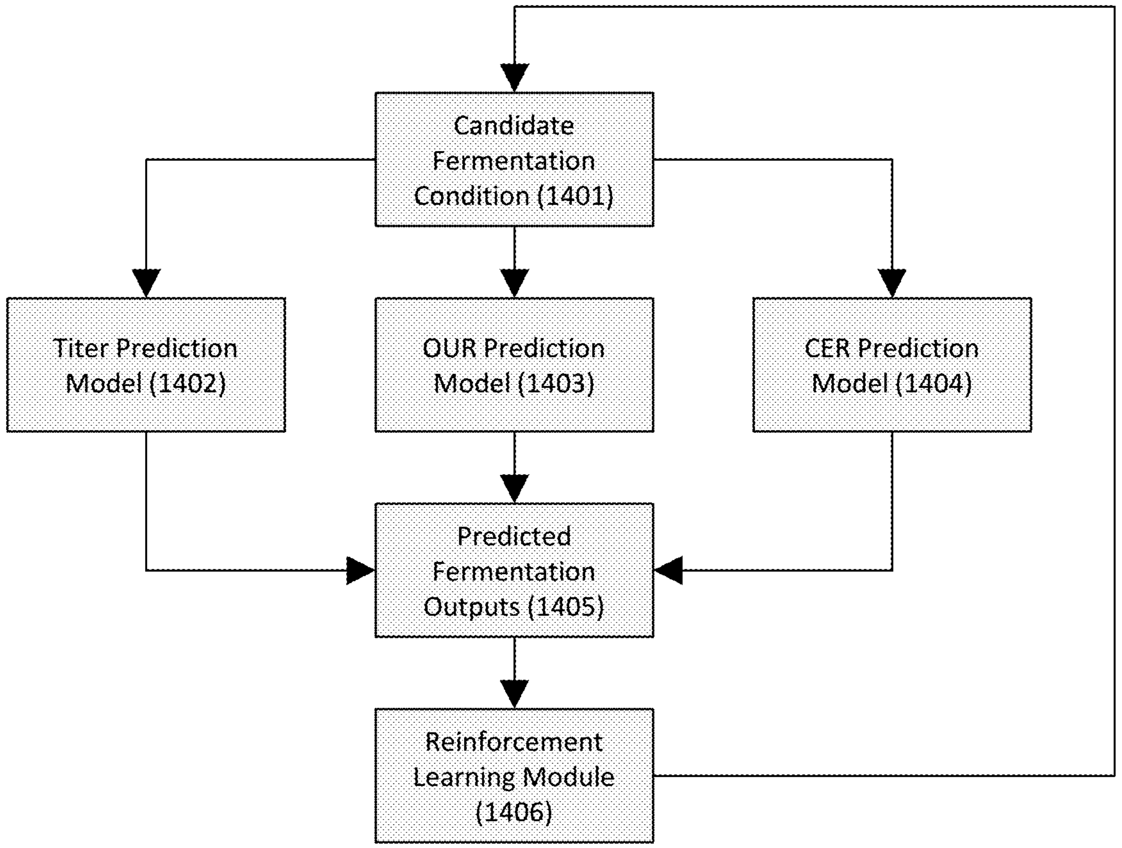
FIG. 14B shows a block diagram of an exemplary method for modeling and process optimization, per one or more embodiments herein.

FIG. 14B shows a block diagram of an exemplary method for modeling and process optimization. As shown, in some embodiments, the method comprises receiving an input of a candidate fermentation condition 1401, which is fed into a titer prediction model 1402, an OUR prediction model 1403, and a CER prediction model 1404. In some embodiments, as shown, the titer prediction model 1402, the OUR prediction model 1403, and the CER prediction model 1404 provide one or more predicted fermentation outputs 1405, which is used for reinforcement of the learning models 1406 by being fed back into the candidate fermentation condition 1401.

In some embodiments, the Adaboost model predictions have a lower absolute error compared to a Neutral Network model. In some embodiments, the Adaboost model may be more accurate in predicting the change in behavior in POI much better than the neutral network model. In some embodiments, the neural network model predicts higher POI than observed for earlier timepoints, but converges towards start of induction. In some embodiments, POI predictions from the neutral network model are higher than those observed for earlier timepoints.

Figure 15A:
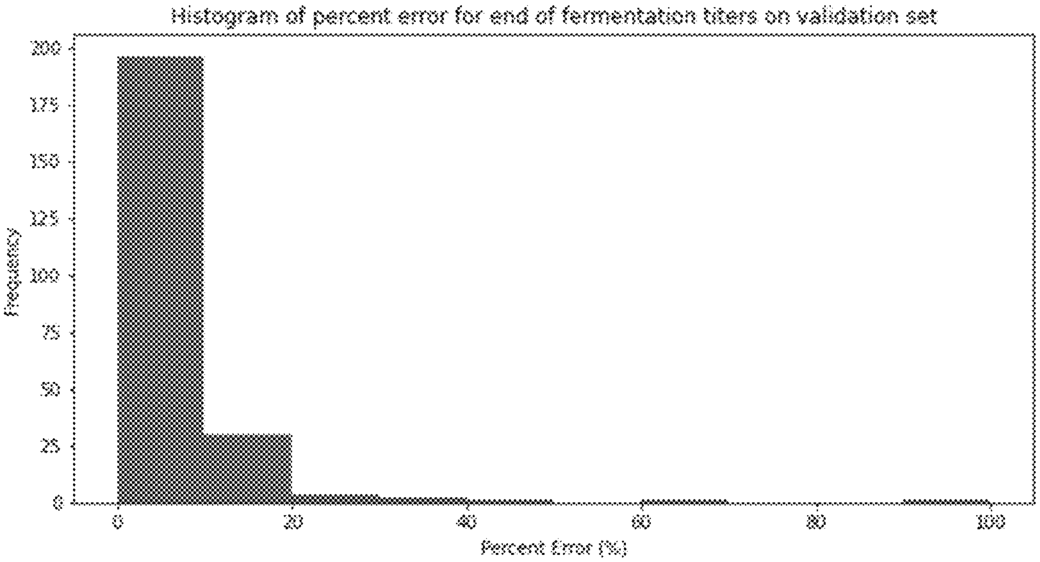
FIG. 15A shows an exemplary graph of percentage errors for end-of-fermentation titer values of a validation set, per one or more embodiments herein.
Figure 15B:
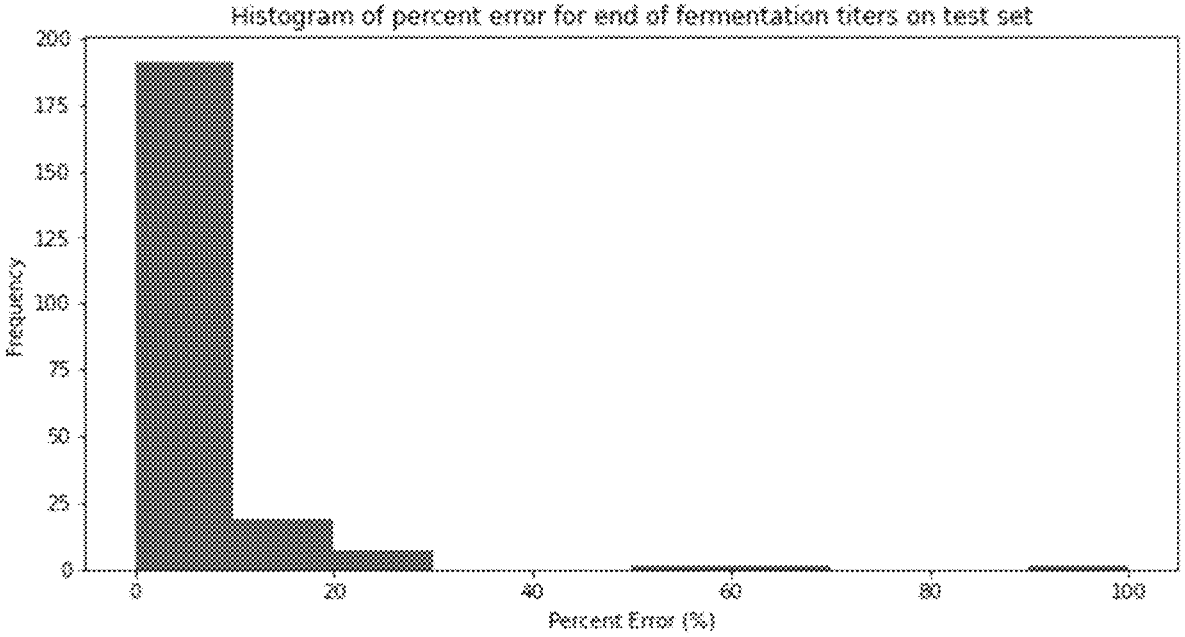
FIG. 15B shows an exemplary graph of percentage errors for end-of-fermentation titer values for test set, per one or more embodiments herein.

FIG. 15A shows an exemplary graph of percentage errors for end-of-fermentation titer values of a validation showing the percentage error values for the validation set. FIG. 15B shows an exemplary graph of percentage errors for end-of-fermentation titer values for a hidden test set. In some embodiments, the methods herein identify fermentation conditions that yield improved outputs. In some embodiments, the methods and systems herein enable a lower methanol feed strategy for improved prediction of fermentation titers. In some embodiments, Adaboost models for predicting HPLC POI titer using fermentation input parameters form predictions based on a validation set and a minimum mean absolute on unseen test data. In some embodiments, Adaboost models for predicting HPLC POI titer using fermentation input parameters form predictions based on a validation set and a maximum mean absolute on unseen test data. In some embodiments, Adaboost is used on a validation set, wherein the results are accepted based on an unseen set performance. As such, in some embodiments, the Adaboost regression machine learning models herein are capable of generalizing and predicting a range of HPLC-based titer values.

Figure 21A:
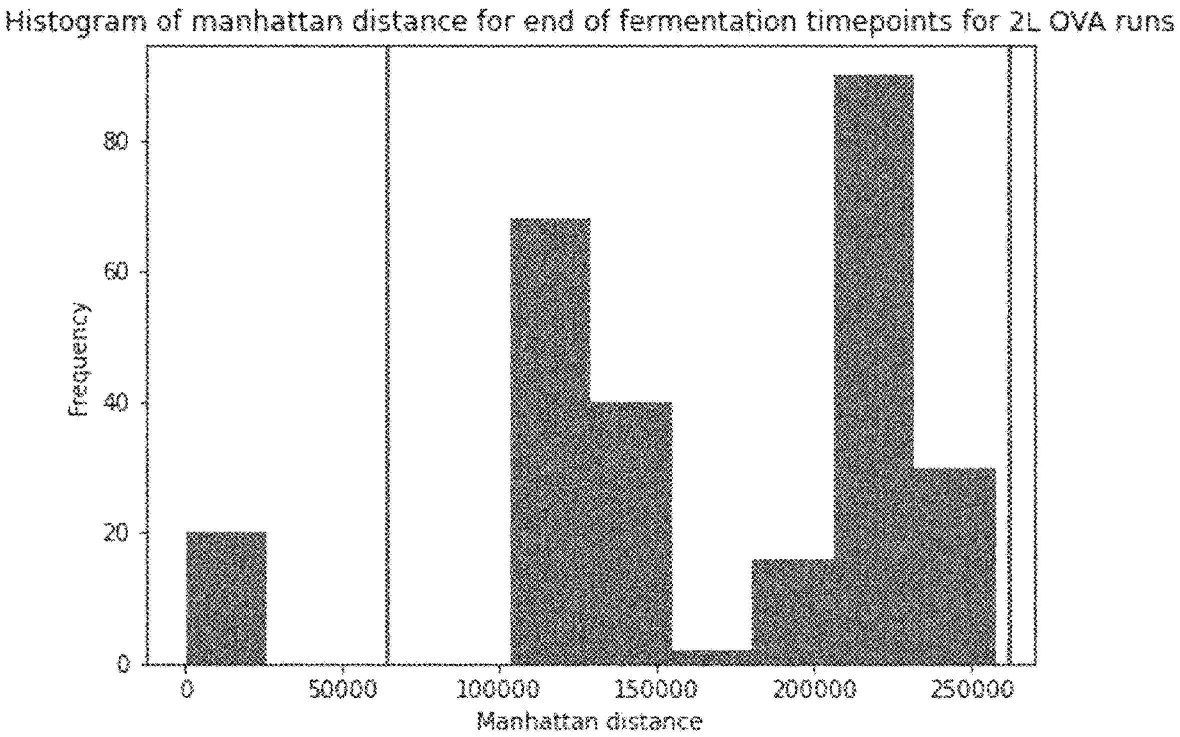
FIG. 21A shows an exemplary histogram of a Manhattan Distance for end-of-file timepoints for Ovalbumin (OVA) runs, per one or more embodiments herein.

FIG. 21A shows an exemplary histogram of a Manhattan Distance for end-of-file timepoints for Ovalbumin (OVA) runs. The two vertical lines therein indicate a cut-off bounds within ±1.5 standard deviations (or about 10%) of the central value, wherein in some embodiments, models herein are trained with "central data" therebetween, and wherein data outside the cut-off bounds represents "extreme" or out-of-sample data, form a hidden set on which predictions are made. As shown, the Adaboost models provides accurate predictions, specifically for the OVA strains at the 2 L scale, even outside the space in which the model has data.

The Manhattan distance between two vectors is equal to the one-norm of the distance between the two vectors. For instance, for two vectors defined as:

$$\vec{A}_\iota=[A_1,A_2,A_3]$$

$$\vec{B}_\iota=[B_1,B_2,B_3]$$

$$\text{Dist}=\text{abs}[A_1-B_1]+\text{abs}[A_2-B_2]+\text{abs}[A_3-B_3]$$

Figure 16:
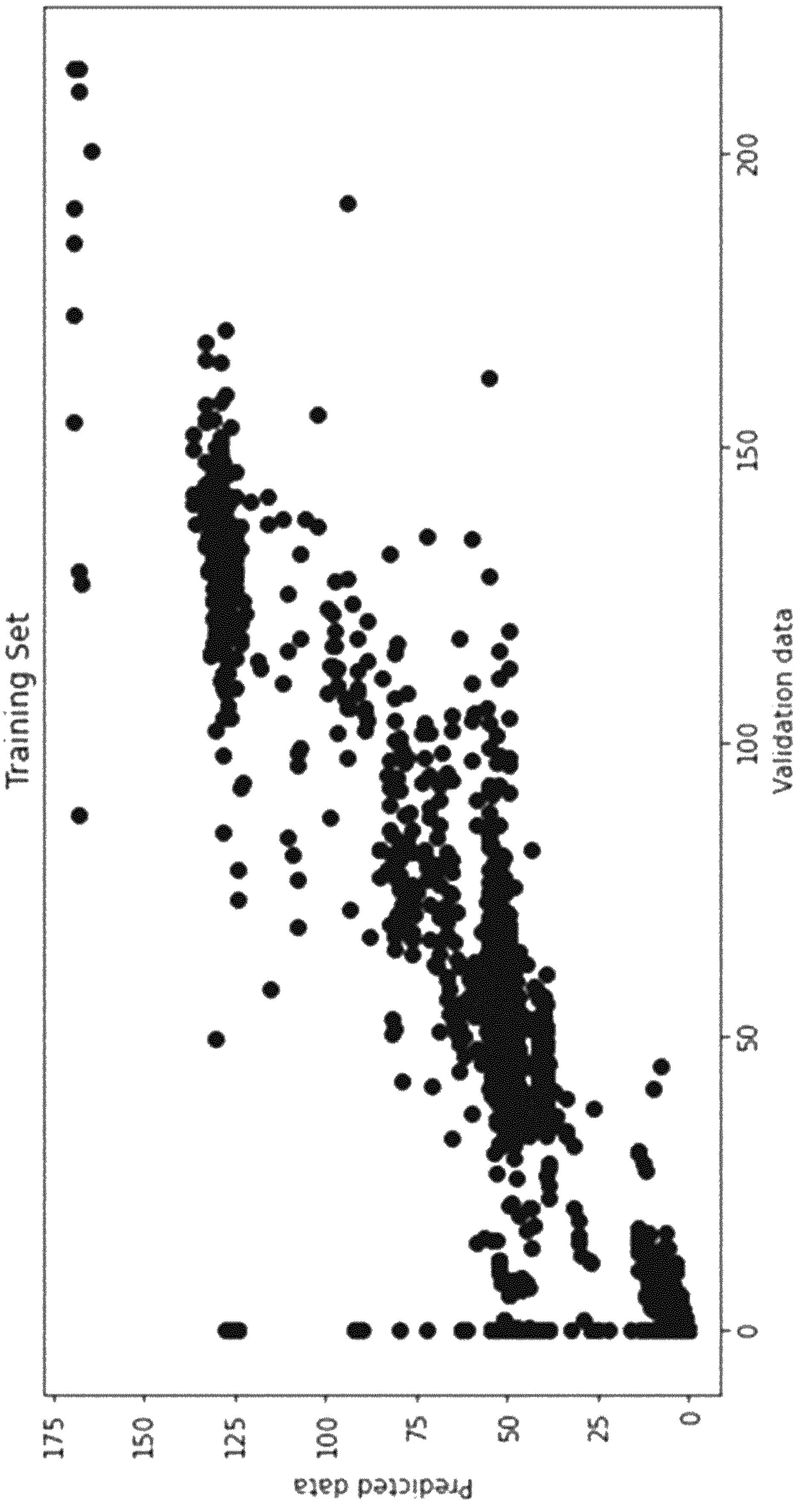
FIG. 16 shows an exemplary scatter plot of validation vs predicted data for a training set with an Adaboost model, per one or more embodiments herein.

FIG. 16 shows an exemplary scatter plot of validation vs predicted data for a training set with an Adaboost model with 47 estimators, exponential loss, a learning rate of about 0.001, and a max depth of 7. As shown, the Adaboost model herein makes accurate prediction for OVA and captures a wide range of values for CER.

Figure 17:
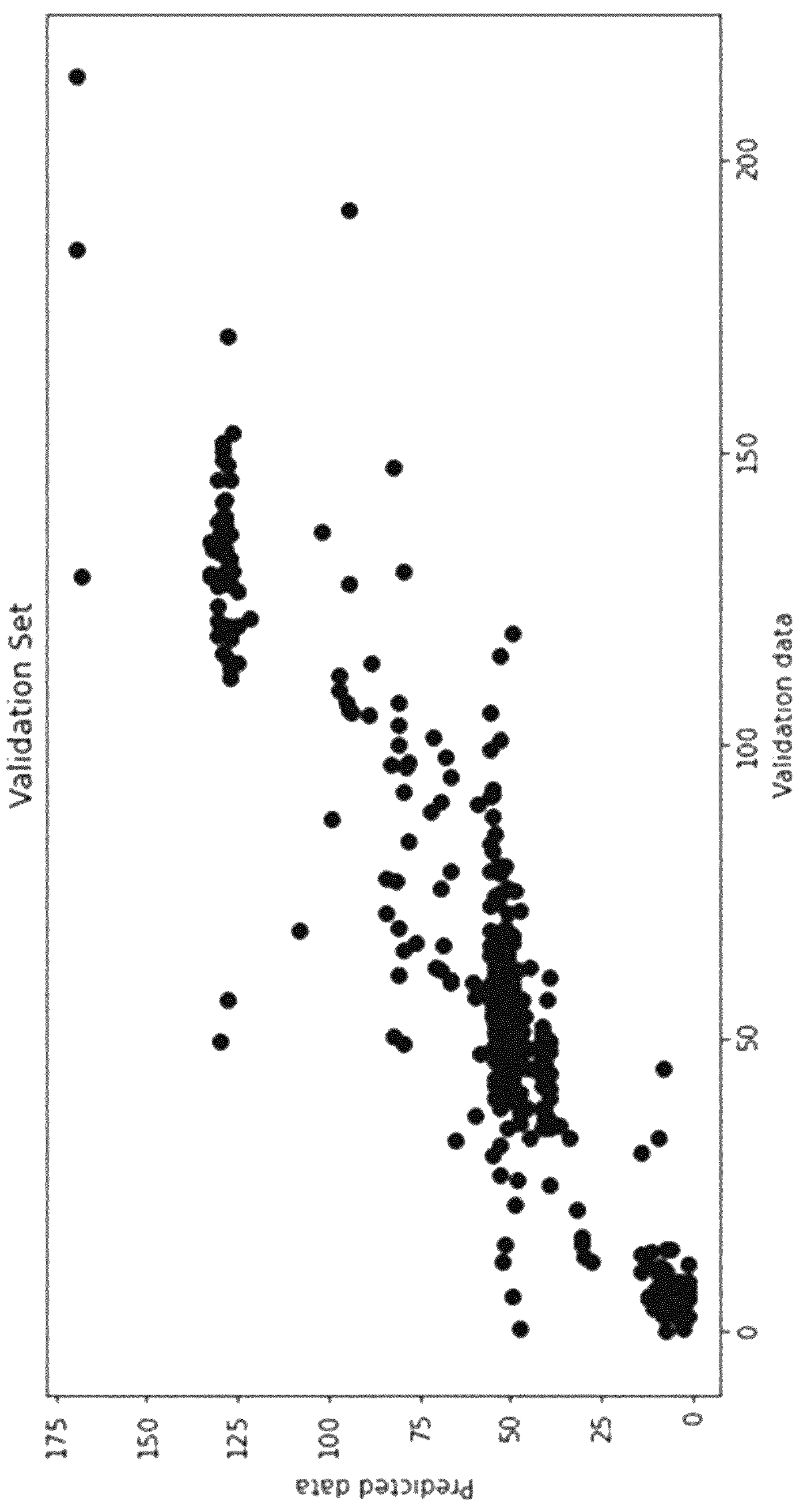
FIG. 17 shows an exemplary scatter plot of validation vs predicted data for a validation set, per one or more embodiments herein.
Figure 18:
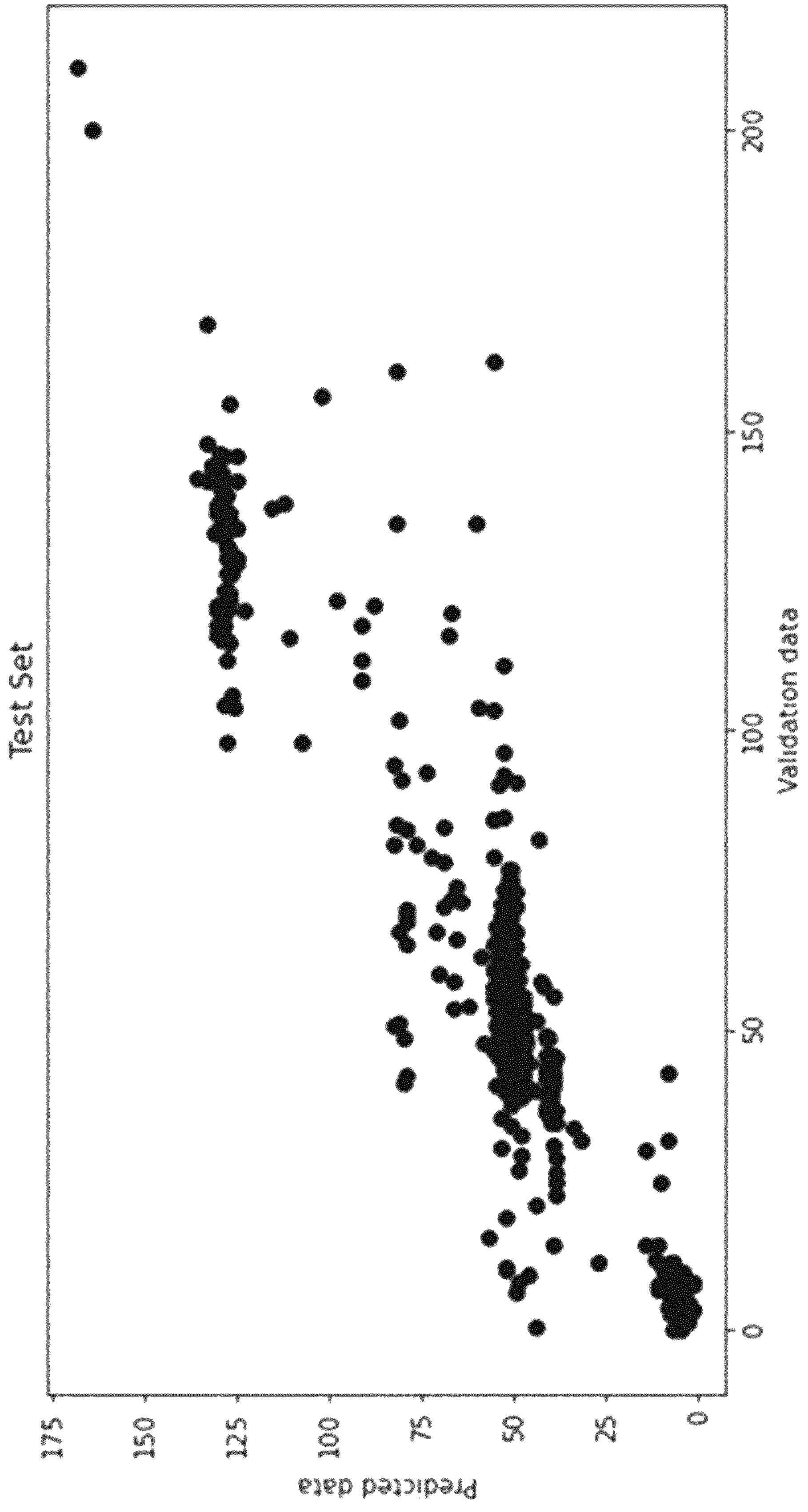
FIG. 18 shows an exemplary scatter plot of validation vs predicted data for a test set, per one or more embodiments herein.
Figure 19:
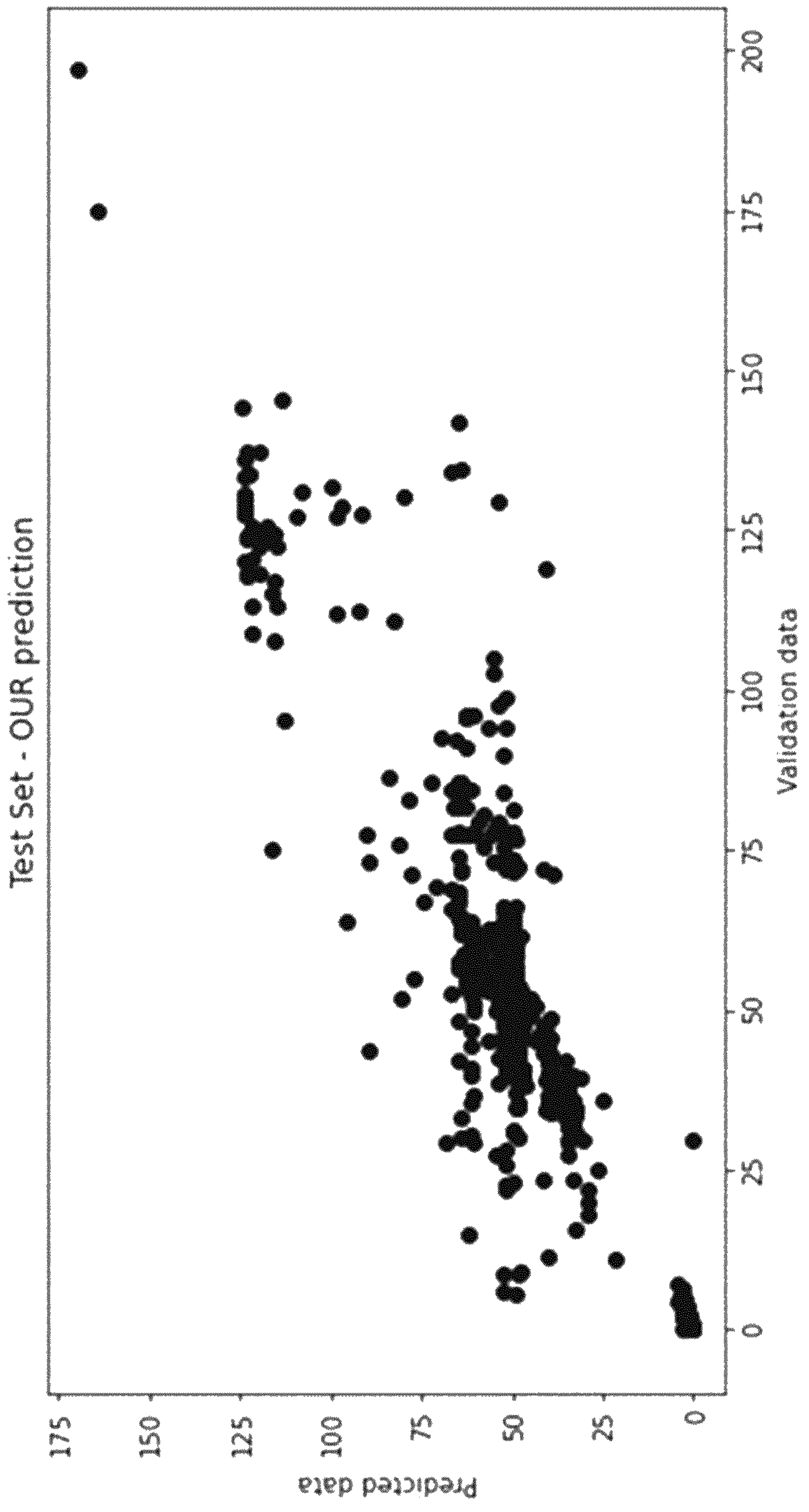
FIG. 19 shows an exemplary scatter plot of validation vs predicted data for a test set trained to predict OUR instead of CER, per one or more embodiments herein.
Figure 20:
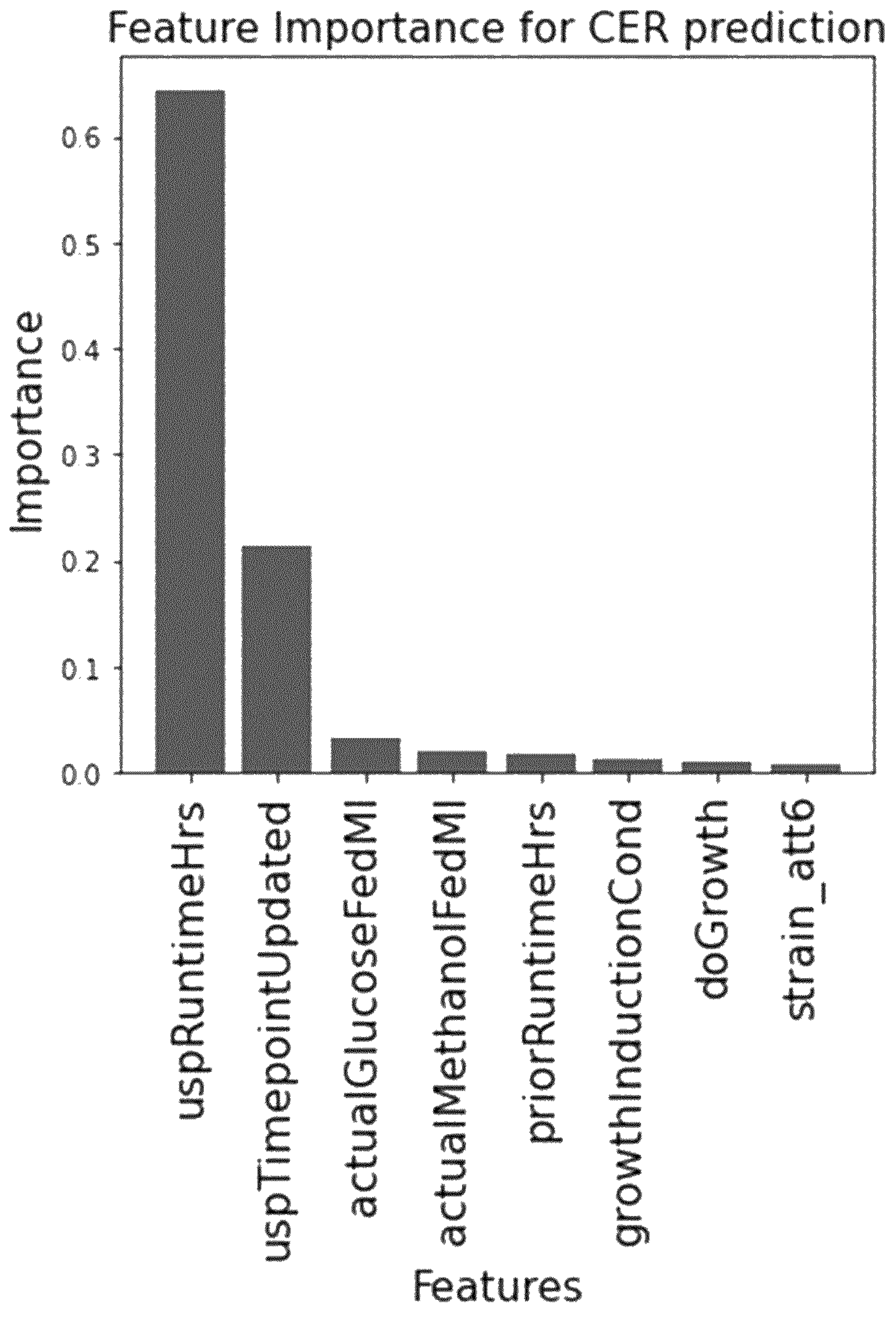
FIG. 20 shows an exemplary bar graph of feature importance for each CER prediction feature, per one or more embodiments herein.

FIG. 17 shows an exemplary scatter plot of validation vs predicted data for a validation set, and FIG. 18 shows an exemplary scatter plot of validation vs predicted data for a test set, wherein the validation and test set contains about 620 data points, with no imputation. As shown, mean absolute error (MAE) on the validation and hidden test sets are slightly lower than training set, implying that the model is able to generalize well and is able to capture a wide range of CER prediction values. FIG. 19 shows an exemplary scatter plot of validation vs predicted data for a test set trained to predict OUR instead of CER. FIG. 20 shows an exemplary bar graph of feature importance for each CER prediction feature. As shown, runtime hours, glucose feed, growth, induction conditions, and methanol feed have a higher importance, which may be due to the fact that the CER (and OUR) is entirely dependent on run time hours, glucose feed as well as the process volume.

Figure 21B:
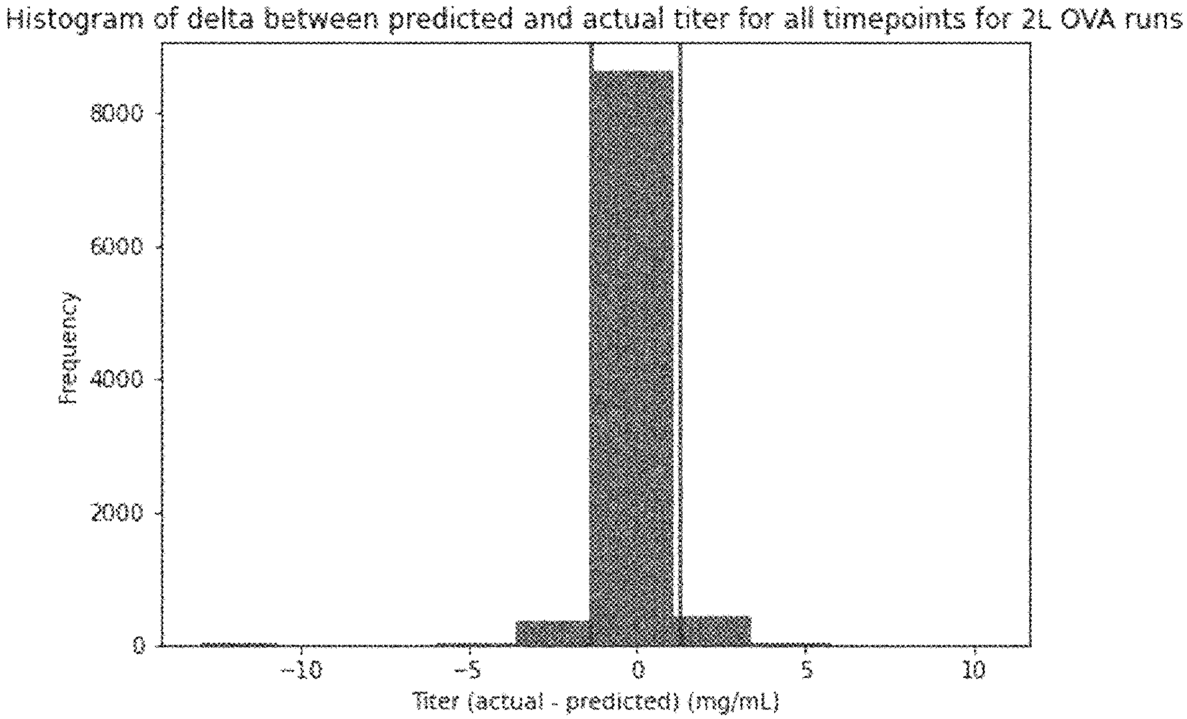
FIG. 21B shows an exemplary histogram of the difference in titers between actual and predicted for all timepoints for 2 L OVA runs, per one or more embodiments herein.

FIG. 21B shows an exemplary histogram of the difference in titers between actual and predicted for all timepoints for 2 L OVA runs, wherein the two vertical lines indicate a central region data points that are within ±1.5 standard deviations of the median difference. Data points within the central region are considered to have a low error, and any data lying outside the central region is considered to have a high error.

Figure 22A:
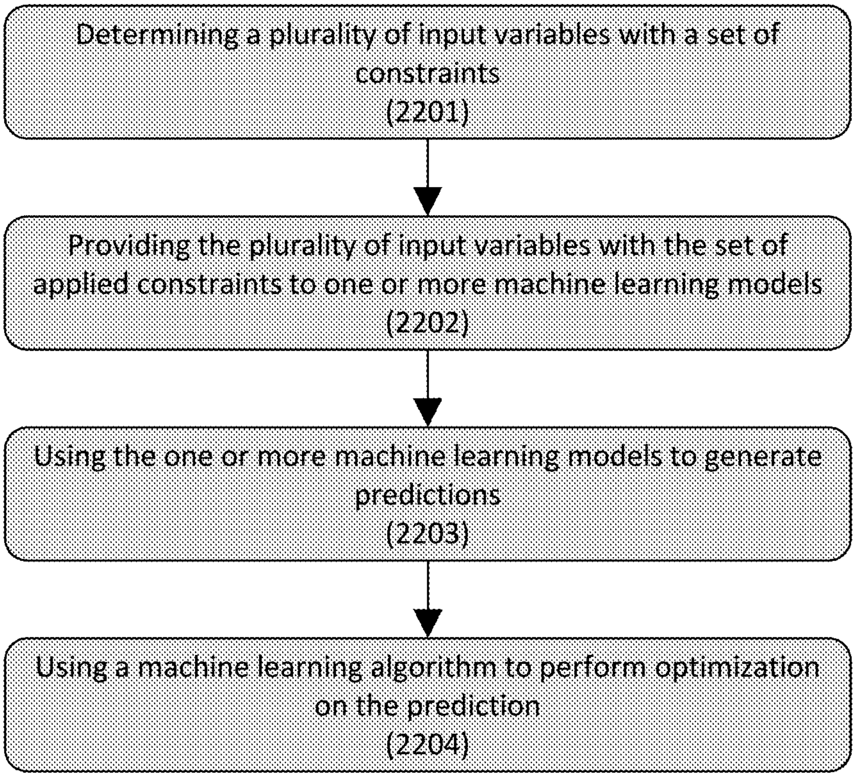
FIG. 22A shows a block diagram of a first exemplary method for fermentation process optimization, per one or more embodiments herein.

FIG. 22A shows a block diagram of a first exemplary method for fermentation process optimization. In some embodiments, the first exemplary method for fermentation process optimization comprises: determining a plurality of input variables with a set of constraints applied thereto 2201, providing the plurality of input variables with the set of applied constraints to one or more machine learning models 2202, using the one or more machine learning models to generate predictions 2203, and using a machine learning algorithm to perform optimization on the prediction 2204.

In some embodiments, the set of constraints relate to one or more physical limitations or processes of a fermentation system. In some embodiments, the one or more physical limitations or processes of the fermentation system comprise at least a container or tank size of the fermentation system, a feed rate, a feed type, or a base media volume. In some embodiments, the one or more physical limitations or processes of the fermentation system comprise one or more constraints on OUR or CER.

In some embodiments, using the one or more machine learning models to generate predictions 2603 comprises using the one or more machine learning models in a first mode or a second mode. In some embodiments, the first mode comprises using a first model to generate a prediction on a given set of input features. In some embodiments, the second mode comprises using the first model and/or an anchor prediction to generate the prediction on the given set of input features and a second model to generate a drag prediction. In some embodiments, the first and second models are different. In some embodiments, the first and second models are congruent. In some embodiments, the first and second models are intended to be used in a complementary manner to each other such that inherent characteristics in decision boundaries in the first and second models are accounted for. In some embodiments, the drag prediction by the second model is used as a datapoint to reduce a prediction error of the primary prediction by the first model. In some embodiments, the first and second models are used as derivative free function approximations of a fermentation process in the fermentation system. In some embodiments, the first model is a decision tree-based model. In some embodiments, the first model comprises an adaptive boosting (AdaBoost) model. In some embodiments, the second model comprises a neural network. In some embodiments, the second model comprises an evolutionary algorithm. In some embodiments, the first model is used to generate one or more out-of-sample predictions on titers that extend beyond or outside of the one or more physical limitations or processes of the fermentation system. In some embodiments, the one or more machine learning models are configured to automatically adapt for a plurality of different sized fermentation systems. In some embodiments, the one or more machine learning models comprises a third model that is configured to predict OUR or CER as a target variable based on the given set of input features. In some embodiments, the given set of input features comprises a subset of features that are accorded relatively higher feature importance weights. In some embodiments, the subset of features comprise runtime, glucose and methanol feed, growth, induction conditions, or dissolved oxygen (DO) growth. In some embodiments, the one or more machine learning models are trained using a training dataset from a fermentation database. In some embodiments, the training dataset comprises at least 50 different features. In some embodiments, the OUR ranges from about 100 mmol/L/hour to 750 mmol/L/hour. In some embodiments, the CER ranges from about 100 mmol/L/hour to 850 mmol/L/hour. In some embodiments, the training dataset comprises at least 5000 data points. In some embodiments, the one or more machine learning models are evaluated or validated based at least on a mean absolute error score using a hidden test set from the fermentation database.

In some embodiments, the feature comprises a quantity of biotin, boric acid, cupric sulfate pentahydrate, ferrous sulfate heptahydrate, manganese sulfate monohydrate, sodium iodide anhydrous, sodium molybdate dihydrate, sulfuric acid, chloride, or any combination thereof in a batch.

In some embodiments, the feature comprises a quantity of biotin, boric acid, cupric sulfate pentahydrate, ferrous sulfate heptahydrate, manganese sulfate monohydrate, sodium iodide anhydrous, sodium molybdate dihydrate, sulfuric acid, zinc chloride, or any combination thereof in a feed provided to the batch.

In some embodiments, the feature comprises a quantity of glucose, methanol, or both fed into the batch at time 0, 1, 2, 3, 4, 5, 6, or 7. In some embodiments, the feature comprises an indication if the batch has a volume of 250 ml, 2 L, or 40 L. In some embodiments, one or more of the features are represented as a binary vector. Other features may include: ammoniumSulfateGl, antifoamFlag, arginineGl, baseMediaVolMl, batchMediaVolMl, biotinGl, boricAcidGl, calciumChlorideDihydrateGl, calcium SulfateDihydrateGl, canolaOilMll, cornOilMll, cupricSulfatePentahydrateGl, dipotassiumPhosphateGl, doGrowth, doInduction, ferrousSulfateHeptahydrateGl, glutamineGl, growthInductionCond, growthPhaseCarbonSourceConc, indicateFinalTimepoint, inductionPhaseCarbonSourceConc, inoculum, isGoodRun, isGrowthGlucose, isGrowthGlycerol, isGrowthIngGlucose, isGrowthNoData, isInductionGlucose, isInductionGlucoseMannose, isInductionGlucoseSorbitol, isInductionGlycerol, isInductionIngGlucose, isInductionMannose, isInductionNoData, isInductionSorbitol, isMajorDeviation, isMinorDeviation, isNoPoiData, isORANGE, isOVA, isOVD, isOVT, isPGA, isdOVA, isgOVL, isoOVA, magnesium SulfateHeptahydrateGl, manganeseSulfateMonohydrateGl, mediaPhosphoricAcidMlL, monoPotassiumPhosphateGl, phGrowth, phInduction, potassiumHydroxideGl, potassiumSulfateGl, sigmaLipidMixtureMll, sodiumIodideAnhydrousGl, sodiumMolybdateDihydrateGl, strain_att0, strain_att1, strain_att2, strain_att3, strain_att4, strain_att5, strain_att6, strain_att7, sulfuricAcidMll, tempGrowth, tempInduction, tudVitaminMixtureMll, uspRuntimeHrs.0, uspRuntimeHrs.1, uspRuntimeHrs.2, uspRuntimeHrs.3, uspRuntimeHrs.4, uspRuntimeHrs.5, uspRuntimeHrs.6, uspRuntimeHrs.7, uspTimepointUpdated, and zincChlorideGl.

In some embodiments, as a genome of a product strain may represent hundreds of thousands of features, direct training of a machine learning algorithm with such data may require millions of measured datapoints. A phylogenetic graph shows relationships between a parent strain and a strain derived therefrom. In some embodiments, the methods and machine learning algorithms herein employ a phylogenetic graph to measure a similarity between strains, enabling a reduced complexity, dimensionally, and required number of measured datapoints. In some embodiments, the methods and machine learning methods herein further employ High-Throughput Screening (HTS) to make a fitted model based on the phylogenic data. In some embodiments, the phylogenic graph is represented as a distance matrix. In some embodiments, the matrix is a sparce adjacency matrix. In some embodiments, the methods herein employ a Multi-Dimensional Scaling (MDS) algorithm, a Principal Component Analysis (PCA), or any combination thereof to further reduce the dimensionality of the phylogenic graphs herein.

In some embodiments, the models herein are configured to maximize titers using an input. In some embodiments, the input comprises a strain, a dimensionally reduced phylogenetic graph location, a HTS calculated assay, an HTS FOIC, a USP runtime, a parent strain titer, a parent HTS calculated assay, a parent FOIC, an indication that the observation includes imputation, or any combination thereof. In some embodiments, the regressor outputs predictions at one or more times. Table 1 below show exemplary regression results for each model validation, wherein the Adaboost model showed the best performance.

TABLE 1

| | MAE | | Hyperparameters | | | |
|---|---|---|---|---|---|---|
| Regression | Train | Valid | Alpha | L2 ratio | Depth | Estimators |
| Adaboost | 1.5 | 2 | | | 6 | 40 |
| Random Forest | 1.8 | 2.2 | | | 4 | 9 |
| Single Tree | 1.7 | 2.4 | | | 5 | |
| Elastic-net | 2.6 | 2.8 | 0.1 | 1 | | |

In some embodiments, the machine learning algorithm perform optimization on the prediction(s) 2604 from the first mode or the second mode. In some embodiments, the machine learning algorithm perform optimization on the prediction(s) 2604 to identify a set of conditions that optimizes or predicts one or more end process targets of the fermentation system for one or more strains of interest. In some embodiments, the one or more end process targets comprise end of fermentation titers. In some embodiments, the set of conditions is used to maximize the end of fermentation titers. In some embodiments, the end of fermentation titers is maximized relative to resource utilization including glucose utilization. In some embodiments, the end of fermentation titers is maximized to be in a range of about 15 to about 50 mg/mL with an Oxygen Uptake Rate (OUR) constraint of up to 850 mmol/L/hour. In some embodiments, the end of fermentation titers is maximized to be at least about 15 mg/mL, 20 mg/mL, 25 mg/mL, 30 mg/mL, 35 mg/mL, 40 mg/mL, or 45 mg/mL, including increments therein. In some embodiments, the end of fermentation titers is maximized to have an OUR constraint of up to about 100 mmol/L/hour, 150 mmol/L/hour, 200 mmol/L/hour, 250 mmol/L/hour, 300 mmol/L/hour, 350 mmol/L/hour, 400 mmol/L/hour, 450 mmol/L/hour, 500 mmol/L/hour, 550 mmol/L/hour, 600 mmol/L/hour, 650 mmol/L/hour, 700 mmol/L/hour, 750 mmol/L/hour, 800 mmol/L/hour, 850 mmol/L/hour, or more including increments therein.

In some embodiments, the machine learning algorithm that is used for the optimization is different from at least one of the machine learning models that are used to generate the prediction(s). In some embodiments, the machine learning algorithm comprises a genetic algorithm. In some embodiments, the genetic algorithm comprises a Non-dominated Sorting Genetic Algorithm (NSGA-II). In some embodiments, the machine learning algorithm is configured to perform the optimization by running a plurality of cycles across a plurality of different run configurations. In some embodiments, a stopping criteria of at least about 0.001 mg/mL is applied to the plurality of cycles. In some embodiments, a stopping criteria of at least about 0.0002 mg/mL, 0.0004 mg/mL, 0.0006 mg/mL, 0.0008 mg/mL, 0.001 mg/mL, 0.0015 mg/mL, or 0.002 mg/mL, including increments therein is applied to the plurality of cycles. In some embodiments, the machine learning algorithm performs the optimization based at least on one or more parameters including number of generations, generation size, mutation rate, crossover probability, or parents' portion to determine offspring. In some embodiments, a median difference in titer between a predicted fermentation titer and an actual titer for a sample fermentation run is within 15%, 14%, 13%, 12%, 11%, 10%, 9%, 8%, 7%, 5%, 4%, 3%, or less, including increments therein.

In some embodiments, the method further comprises using the identified set of conditions to modify one or more of the following: media, pH, duration of fermentation cycle, temperature, feed rate, filtration for one or more impurities, agitation or stirring rate, oxygen uptake, or carbon dioxide generation.

Figure 22B:
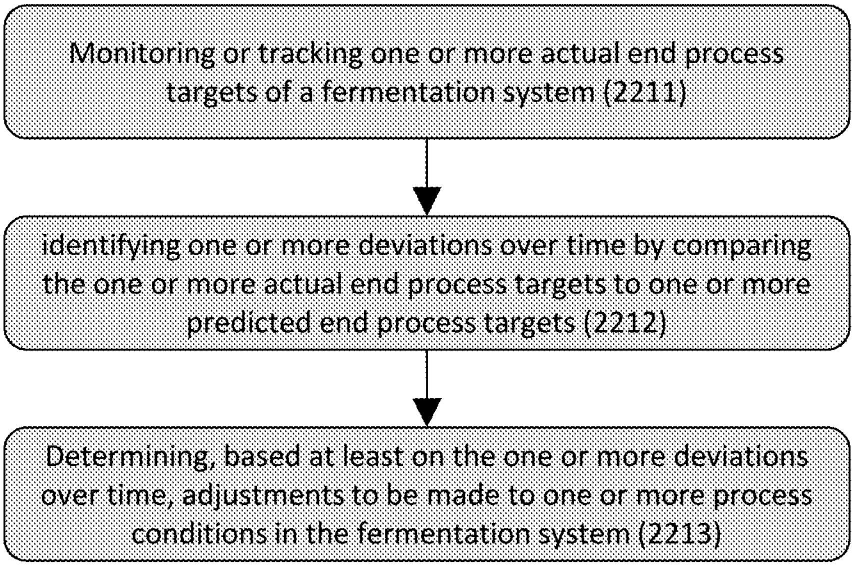
FIG. 22B shows a block diagram of a second exemplary method for fermentation process optimization, per one or more embodiments herein.

FIG. 22B shows a block diagram of a second exemplary method for fermentation process optimization. As shown, the method comprises monitoring or tracking one or more actual end process targets of a fermentation system 2211, identifying one or more deviations over time by comparing the one or more actual end process targets to one or more predicted end process targets 2212, and determining, based at least on the one or more deviations over time, adjustments to be made to one or more process conditions in the fermentation system 2213.

In some embodiments, the one or more predicted end process targets are predicted using one or more machine learning models that are useable in a first mode or a second mode. In some embodiments, the first mode comprises using a first model to generate a prediction on a given set of input features. In some embodiments, the second mode comprises using the first model and/or an anchor prediction to generate the prediction on the given set of input features and a second model to generate a drag prediction. In some embodiments, the first and second models are different. In some embodiments, the first and second models are intended to be used in a complementary manner to each other such that inherent characteristics in decision boundaries in the first and second models are accounted for. In some embodiments, the drag prediction by the second model is used as a datapoint to reduce a prediction error of the primary prediction by the first model. In some embodiments, the first and second models are used as derivative free function approximations of a fermentation process in the fermentation system. In some embodiments, the first model is a decision tree-based model. In some embodiments, the first model comprises an adaptive boosting (AdaBoost) model. In some embodiments, the second model comprises a neural network. In some embodiments, the second model comprises an evolutionary algorithm.

In some embodiments, the one or more predicted end process targets are optimized by a machine learning algorithm. In some embodiments, the machine learning algorithm that is used for the optimization is different from at least one of the machine learning models that are used to generate the prediction(s). In some embodiments, the machine learning algorithm comprises a genetic algorithm. In some embodiments, the genetic algorithm comprises a Non-dominated Sorting Genetic Algorithm (NSGA-II). In some embodiments, the one or more end process targets relate to cell viability. In some embodiments, the set of conditions is used to maximize the cell viability. In some embodiments, the one or more actual end process targets comprise measured cell viability, and the one or more predicted end process targets comprise predicted cell viability that are predicted using the one or more machine learning models. In some embodiments, optimizing the one or more actual end process targets comprise maximizing the measured cell viability for the one or more subsequent batch runs. In some embodiments, optimizing the one or more actual end process targets comprises making the adjustments to the one or more process conditions, to ensure that a number of cells per volume of media for the one or more subsequent batch runs does not fall below a predefined threshold. In some embodiments, the more actual end process targets comprise an operational cost and/or a cycle time for running the fermentation system.

In some embodiments, the adjustments to be made to one or more process conditions in the fermentation system are determined based at least on the one or more deviations over time to optimize the one or more actual end process targets in one or more subsequent batch runs. In some embodiments, the one or more process conditions comprise media, pH, duration of fermentation cycle, temperature, feed rate, filtration for one or more impurities, agitation or stirring rate, oxygen uptake, or carbon dioxide generation. In some embodiments, the adjustments are dynamically made to the one or more process conditions in real-time. In some embodiments, the one or more process conditions comprises a set of upstream process conditions in the fermentation system. In some embodiments, the one or more process conditions comprises a set of downstream process conditions in the fermentation system. In some embodiments, the one or more actual end process targets comprise measured end of fermentation titers, and the one or more predicted end process targets comprise predicted end of fermentation titers that are predicted using the one or more machine learning models. In some embodiments, optimizing the one or more actual end process targets comprise maximizing the measured end of fermentation titers for the one or more subsequent batch runs.

In some embodiments, the method further comprises continuously making the adjustments to the one or more process conditions for the one or more subsequent batch runs as the fermentation system is operating.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" in some cases refers to an amount that is approximately the stated amount. As used herein, the term "about" refers to an amount that is near the stated amount by 10%, 5%, or 1%, including increments therein. As used herein, the term "about" in reference to a percentage refers to an amount that is greater or less the stated percentage by 10%, 5%, or 1%, including increments therein. Where particular values are described in the application and claims, unless otherwise stated the term "about" should be assumed to mean an acceptable error range for the particular value. In some instances, the term "about" also includes the particular value. For example, "about 5" includes 5.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, the term "comprise" or variations thereof such as "comprises" or "comprising" are to be read to indicate the inclusion of any recited feature but not the exclusion of any other features. Thus, as used herein, the term "comprising" is inclusive and does not exclude additional, unrecited features. In some embodiments of any of the compositions and methods provided herein, "comprising" may be replaced with "consisting essentially of" or "consisting of." The phrase "consisting essentially of" is used herein to require the specified feature(s) as well as those which do not materially affect the character or function of the claimed disclosure. As used herein, the term "consisting" is used to indicate the presence of the recited feature alone.

Any aspect or embodiment described herein may be combined with any other aspect or embodiment as disclosed herein.

Computing System

Figure 23:
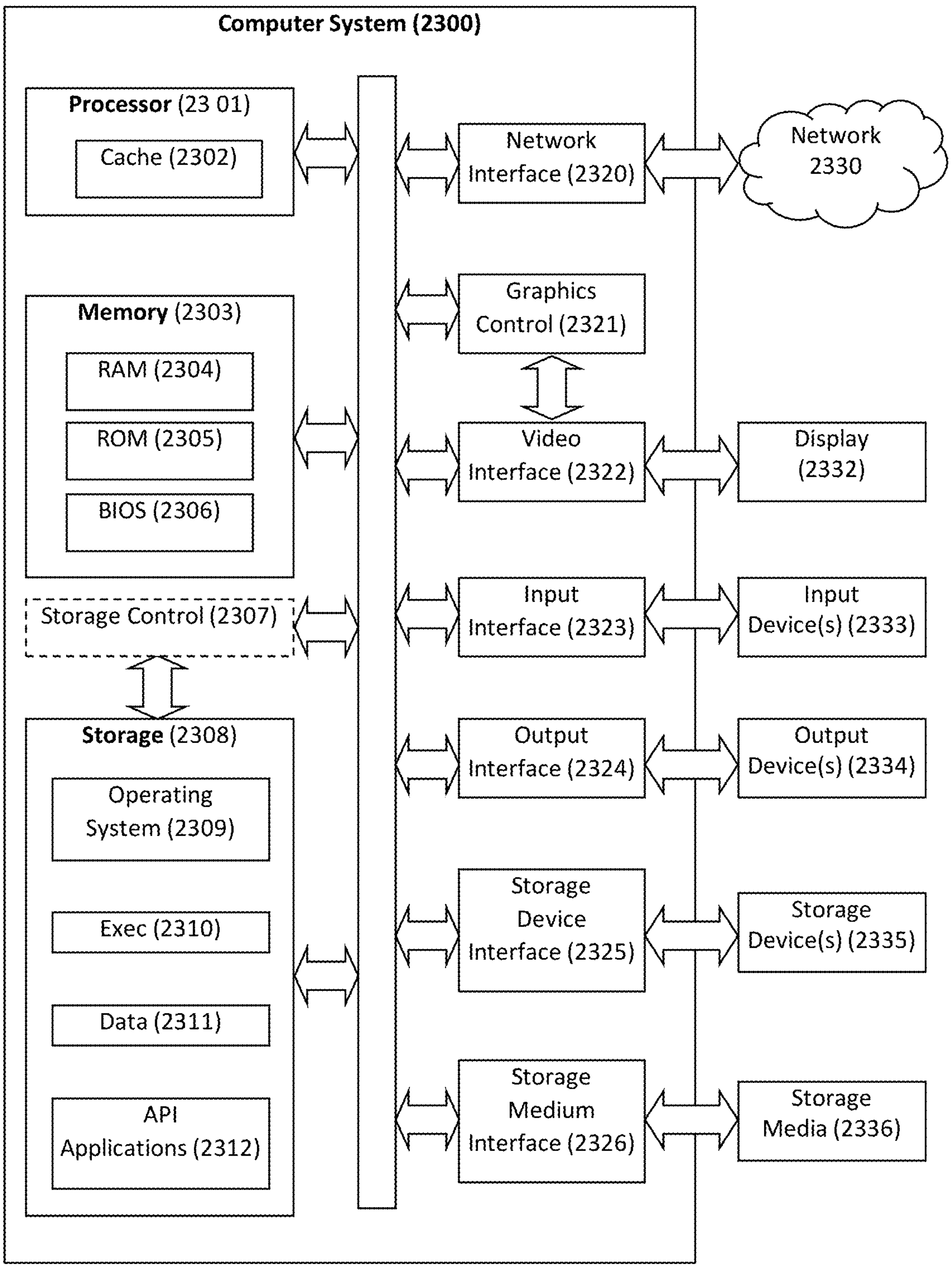
FIG. 23 shows a non-limiting example of a computing device; in this case, a device with one or more processors, memory, storage, and a network interface, per one or more embodiments herein.

Referring to FIG. 23, a block diagram is shown depicting an exemplary machine that includes a computer system 2300 (e.g., a processing or computing system) within which a set of instructions may execute for causing a device to perform or execute any one or more of the aspects and/or methodologies for static code scheduling of the present disclosure. The components in FIG. 23 are examples only and do not limit the scope of use or functionality of any hardware, software, embedded logic component, or a combination of two or more such components implementing particular embodiments.

Computer system 2300 may include one or more processors 2301, a memory 2303, and a storage 2308 that communicate with each other, and with other components, via a bus 2340. The bus 2340 may also link a display 2332, one or more input devices 2333 (which may, for example, include a keypad, a keyboard, a mouse, a stylus, etc.), one or more output devices 2334, one or more storage devices 2335, and various tangible storage media 2336. All of these elements may interface directly or via one or more interfaces or adaptors to the bus 2340. For instance, the various tangible storage media 2336 may interface with the bus 2340 via storage medium interface 2326. Computer system 2300 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 2300 includes one or more processor(s) 2301 (e.g., central processing units (CPUs) or general purpose graphics processing units (GPGPUs)) that carry out functions. Processor(s) 2301 optionally contains a cache memory unit 2302 for temporary local storage of instructions, data, or computer addresses. Processor(s) 2301 are configured to assist in execution of computer readable instructions. Computer system 2300 may provide functionality for the components depicted in FIG. 23 as a result of the processor(s) 2301 executing non-transitory, processor-executable instructions embodied in one or more tangible computer-readable storage media, such as memory 2303, storage 2308, storage devices 2335, and/or storage medium 2336. The computer-readable media may store software that implements particular embodiments, and processor(s) 2301 may execute the software. Memory 2303 may read the software from one or more other computer-readable media (such as mass storage device(s) 2335, 2336) or from one or more other sources through a suitable interface, such as network interface 2320. The software may cause processor (s) 2301 to carry out one or more processes or one or more steps of one or more processes described or illustrated herein. Carrying out such processes or steps may include defining data structures stored in memory 2303 and modifying the data structures as directed by the software.

The memory 2303 may include various components (e.g., machine readable media) including, but not limited to, a random access memory component (e.g., RAM 2304) (e.g., static RAM (SRAM), dynamic RAM (DRAM), ferroelectric random access memory (FRAM), phase-change random access memory (PRAM), etc.), a read-only memory component (e.g., ROM 2305), and any combinations thereof. ROM 2305 may act to communicate data and instructions unidirectionally to processor(s) 2301, and RAM 2304 may act to communicate data and instructions bidirectionally with processor(s) 2301. ROM 2305 and RAM 2304 may include any suitable tangible computer-readable media described below. In one example, a basic input/output system 2306 (BIOS), including basic routines that help to transfer information between elements within computer system 2300, such as during start-up, may be stored in the memory 2303.

Fixed storage 2308 is connected bidirectionally to processor(s) 2301, optionally through storage control unit 2307.

Fixed storage 2308 provides additional data storage capacity and may also include any suitable tangible computer-readable media described herein. Storage 2308 may be used to store operating system 2309, executable(s) 2310, data 2311, applications 2312 (application programs), and the like. Storage 2308 may also include an optical disk drive, a solid-state memory device (e.g., flash-based systems), or a combination of any of the above. Information in storage 2308 may, in appropriate cases, be incorporated as virtual memory in memory 2303.

In one example, storage device(s) 2335 may be removably interfaced with computer system 2300 (e.g., via an external port connector (not shown)) via a storage device interface 2325. Particularly, storage device(s) 2335 and an associated machine-readable medium may provide non-volatile and/or volatile storage of machine-readable instructions, data structures, program modules, and/or other data for the computer system 2300. In one example, software may reside, completely or partially, within a machine-readable medium on storage device(s) 2335. In another example, software may reside, completely or partially, within processor(s) 2301.

Bus 2340 connects a wide variety of subsystems. Herein, reference to a bus may encompass one or more digital signal lines serving a common function, where appropriate. Bus 2340 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 2300 may also include an input device 2333. In one example, a user of computer system 2300 may enter commands and/or other information into computer system 2300 via input device(s) 2333. Examples of an input device(s) 2333 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 2333 may be interfaced to bus 2340 via any of a variety of input interfaces 2323 (e.g., input interface 2323) including, but not limited to, serial, parallel, game port, USB, FIREWIRE, THUNDERBOLT, or any combination of the above.

In particular embodiments, when computer system 2300 is connected to network 2330, computer system 2300 may communicate with other devices, specifically mobile devices and enterprise systems, distributed computing systems, cloud storage systems, cloud computing systems, and the like, connected to network 2330. Communications to and from computer system 2300 may be sent through network interface 2320. For example, network interface 2320 may receive incoming communications (such as requests or responses from other devices) in the form of one or more packets (such as Internet Protocol (IP) packets) from network 2330, and computer system 2300 may store the incoming communications in memory 2303 for processing. Computer system 2300 may similarly store outgoing communications (such as requests or responses to other devices) in the form of one or more packets in memory 2303 and communicated to network 2330 from network interface 2320. Processor(s) 2301 may access these communication packets stored in memory 2303 for processing.

Examples of the network interface 2320 include, but are not limited to, a network interface card, a modem, and any combination thereof. Examples of a network 2330 or network segment 2330 include, but are not limited to, a distributed computing system, a cloud computing system, a wide area network (WAN) (e.g., the Internet, an enterprise network), a local area network (LAN) (e.g., a network associated with an office, a building, a campus, or other relatively small geographic space), a telephone network, a direct connection between two computing devices, a peer-to-peer network, and any combinations thereof. A network, such as network 2330, may employ a wired and/or a wireless mode of communication. In general, any network topology may be used.

Information and data may be displayed through a display 2332. Examples of a display 2332 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 2332 may interface to the processor(s) 2301, memory 2303, and fixed storage 2308, as well as other devices, such as input device(s) 2333, via the bus 2340. The display 2332 is linked to the bus 2340 via a video interface 2322, and transport of data between the display 2332 and the bus 2340 may be controlled via the graphics control 2321. In some embodiments, the display is a video projector. In some embodiments, the display is a head-mounted display (HMD) such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In addition to a display 2332, computer system 2300 may include one or more other peripheral output devices 2334 including, but not limited to, an audio speaker, a printer, a storage device, and any combinations thereof. Such peripheral output devices may be connected to the bus 2340 via an output interface 2324. Examples of an output interface 2324 include, but are not limited to, a serial port, a parallel connection, a USB port, a FIREWIRE port, a THUNDERBOLT port, and any combinations thereof.

In addition or as an alternative, computer system 2300 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a downstream processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor may read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will also recognize that select televisions, video players, and digital music players with optional computer network connectivity are suitable for use in the system described herein. Suitable tablet computers, in various embodiments, include those with booklet, slate, and convertible configurations, known to those of skill in the art.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® P53®, Sony® P54®, Microsoft® Xbox 360®, Microsoft Xbox One, Nintendo® Wii®, Nintendo® Wii U®, and Ouya®.

Non-Transitory Computer Readable Storage Medium

In some embodiments, the platforms, systems, media, and methods disclosed herein include one or more non-transitory computer readable storage media encoded with a program including instructions executable by the operating system of an optionally networked computing device. In further embodiments, a computer readable storage medium is a tangible component of a computing device. In still further embodiments, a computer readable storage medium is optionally removable from a computing device. In some embodiments, a computer readable storage medium includes, by way of non-limiting examples, CD-ROMs, DVDs, flash memory devices, solid state memory, magnetic disk drives, magnetic tape drives, optical disk drives, distributed computing systems including cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Figure 24:
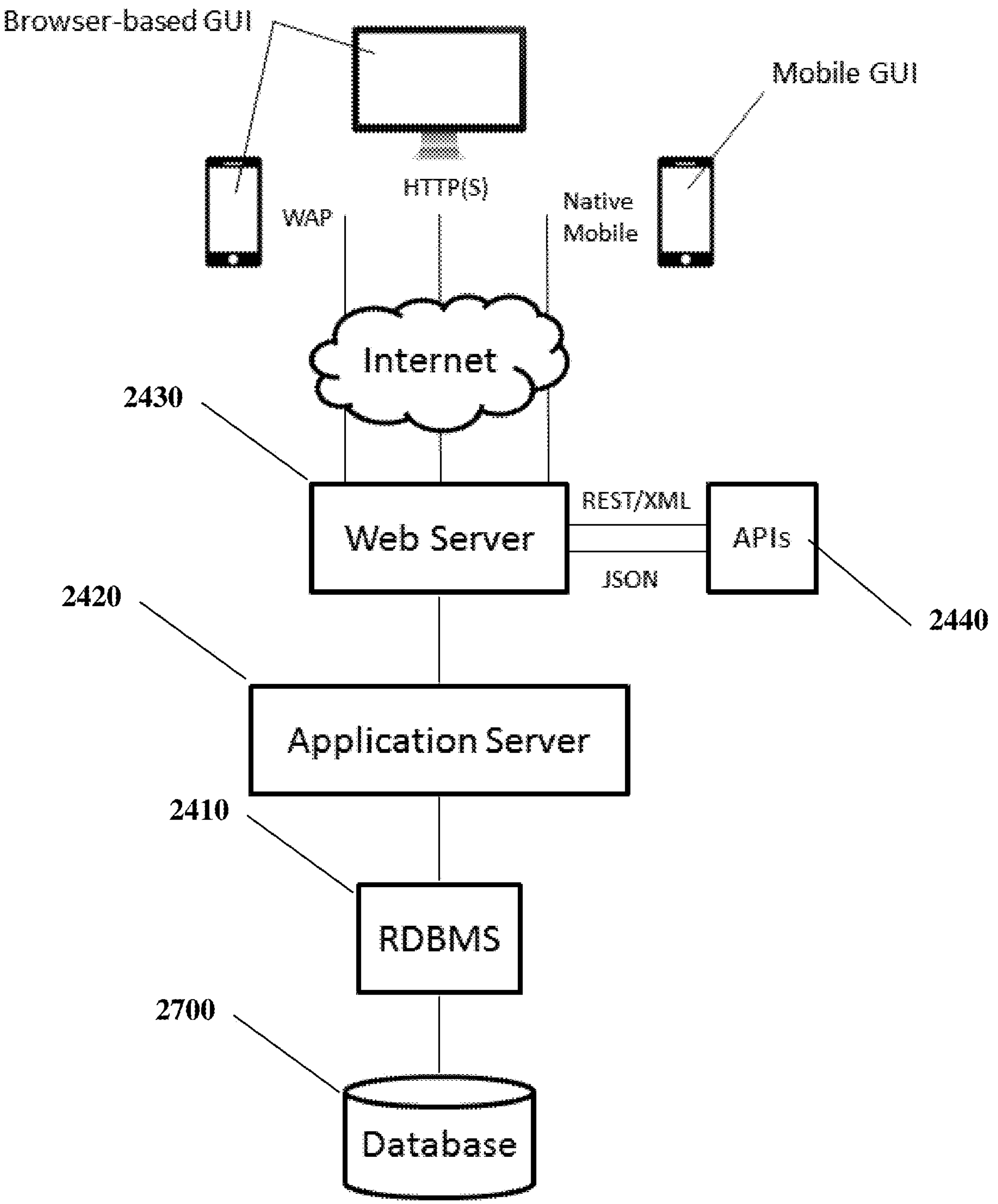
FIG. 24 shows a non-limiting example of a web/mobile application provision system; in this case, a system providing browser-based and/or native mobile user interfaces, per one or more embodiments herein.

Referring to FIG. 24, in a particular embodiment, an application provision system comprises one or more databases 2400 accessed by a relational database management system (RDBMS) 2410. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 2420 (such as Java servers, .NET servers, PHP servers, and the like) and one or more web servers 2430 (such as Apache, IIS, GWS and the like). The web server(s) optionally expose one or more web services via app application programming interfaces (APIs) 2440. Via a network, such as the Internet, the system provides browser-based and/or mobile native user interfaces.

Figure 25:
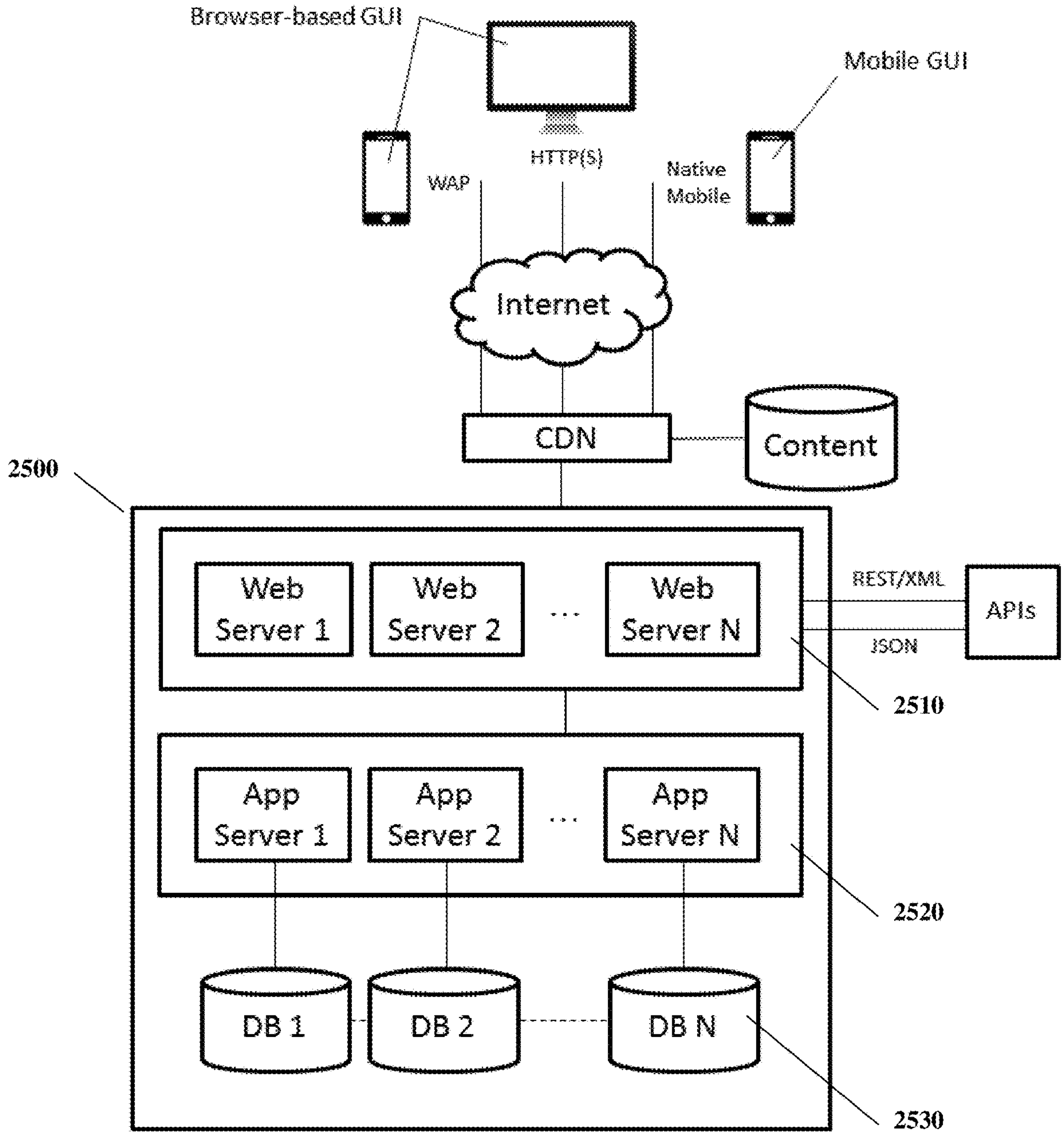
FIG. 25 shows a non-limiting example of a cloud-based web/mobile application provision system; in this case, a system comprising an elastically load balanced, auto-scaling web server and application server resources as well synchronously replicated databases, per one or more embodiments herein.

Referring to FIG. 25, in a particular embodiment, an application provision system alternatively has a distributed, cloud-based architecture 2500 and comprises elastically load balanced, auto-scaling web server resources 2510 and application server resources 2520 as well synchronously replicated databases 2530.

Mobile Application

In some embodiments, a computer program includes a mobile application provided to a mobile computing device. In some embodiments, the mobile application is provided to a mobile computing device at the time it is manufactured. In other embodiments, the mobile application is provided to a mobile computing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome Web Store, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB.NET, or combinations thereof. Compilation is often performed, at least in part, to create an executable program. In some embodiments, a computer program includes one or more executable complied applications.

Web Browser Plug-in

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, may for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ PHP, Python™, and VB.NET, or combinations thereof.

Web browsers (also called Internet browsers) are software applications, designed for use with network-connected computing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called microbrowsers, mini-browsers, and wireless browsers) are designed for use on mobile computing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of analytical, strain, genomics, process, fermentation, recovery, quality, sensory, functional property, commercial, demand, user, subscription, log, machine characteristic, and human actions data information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In a particular embodiment, a database is a distributed database. In other embodiments, a database is based on one or more local computer storage devices.

Machine Learning

In some embodiments, the machine learning algorithms herein employ one or more forms of labels including but not limited to human annotated labels and semi-supervised labels. In some embodiments, the machine learning algorithm utilizes regression modeling, wherein relationships between predictor variables and dependent variables are determined and weighted.

The human annotated labels may be provided by a hand-crafted heuristic. The semi-supervised labels may be determined using a clustering technique to find properties similar to those flagged by previous human annotated labels and previous semi-supervised labels. The semi-supervised labels may employ a XGBoost, a neural network, or both.

A distant supervision method may create a large training set seeded by a small hand-annotated training set. The distant supervision method may comprise positive-unlabeled learning with the training set as the 'positive' class. The distant supervision method may employ a logistic regression model, a recurrent neural network, or both. The recurrent neural network may be advantageous for Natural Language Processing (NLP) machine learning.

Examples of machine learning algorithms may include a support vector machine (SVM), a naïve Bayes classification, a random forest, a neural network, deep learning, or other supervised learning algorithm or unsupervised learning algorithm for classification and regression. The machine learning algorithms may be trained using one or more training datasets.

In some embodiments, a machine learning algorithm is used to predict titer times. A non-limiting example of a multi-variate linear regression model algorithm is seen below: probability=$A_0+A_1$ $(X_1)+A_2(X_2)+A_3(X_3)+A_4(X_4)+A_5(X_5)+A_6(X_6)+A_7(X_7)$ . . . wherein $A_i$ ($A_1, A_2, A_3, A_4, A_5, A_6, A_7, \ldots$) are "weights" or coefficients found during the regression modeling; and $X_i$ ($X_1, X_2, X_3, X_4, X_5, X_6, X_7, \ldots$) are data collected from prior production runs. Any number of $A_i$ and $X_i$ variable may be included in the model. In some embodiments, the programming language "R" is used to run the model.

What is claimed is:

1. A method for fermentation process optimization, comprising:

determining a plurality of input variables with a set of constraints applied thereto, wherein the set of constraints relate to one or more physical limitations or processes of a fermentation system; providing the plurality of input variables with the set of applied constraints to one or more machine learning models;

using the one or more machine learning models in a first mode or a second mode, wherein the first mode comprises using a first model to generate a prediction on a given set of input features, and the second mode comprises using the first model and/or an anchor prediction to generate the prediction on the given set of input features and a second model to generate a drag prediction, wherein the drag prediction by the second model is used as a datapoint to reduce a prediction error of the primary prediction by the first model; and using a machine learning algorithm to perform optimization on the prediction(s) from the first mode or the second mode, to identify a set of conditions that optimizes or predicts one or more end process targets of the fermentation system for one or more strains of interest.

2. The method of claim 1, wherein the one or more physical limitations or processes of the fermentation system comprise at least a container or tank size of the fermentation system, a feed rate, a feed type, or a base media volume.

3. The method of claim 1, wherein the one or more physical limitations or processes of the fermentation system comprise one or more constraints on oxygen uptake rate (OUR) or Carbon Dioxide Evolution Rate (CER).

4. The method of claim 1, comprising: using the identified set of conditions to modify one or more of the following: media, pH, duration of fermentation cycle, temperature, feed rate, filtration for one or more impurities, agitation or stirring rate, oxygen uptake, or carbon dioxide generation.

5. The method of claim 1, wherein the one or more end process targets comprise end of fermentation titers.

6. The method of claim 5, wherein the set of conditions is used to maximize the end of fermentation titers.

7. The method of claim 6, wherein the end of fermentation titers is maximized relative to resource utilization including glucose utilization.

8. The method of claim 6, wherein the end of fermentation titers is maximized to be in a range of about 15 to about 50 mg/ml with an OUR constraint of up to about 750 mmol/L/hour.

9. The method of claim 1, wherein the first and second models are different.

10. The method of claim 8, wherein the first and second models are intended to be used in a complementary manner to each other such that inherent characteristics in decision boundaries in the first and second models are accounted for.

11. The method of claim 1, wherein the first and second models are used as derivative free function approximations of a fermentation process in the fermentation system.

12. The method of claim 1, wherein the first model is a decision tree-based model.

13. The method of claim 1, wherein the first model comprises an adaptive boosting (Ada Boost) model.

14. The method of claim 1, wherein the second model comprises a neural network.

15. The method of claim 1, wherein the second model comprises an evolutionary algorithm.

16. The method of claim 1, wherein the machine learning algorithm that is used for the optimization is different from at least one of the machine learning models that are used to generate the prediction(s).

17. The method of claim 1, wherein the machine learning algorithm comprises a genetic algorithm.

18. The method of claim 16, wherein the genetic algorithm comprises a Non-dominated Sorting Genetic Algorithm (NSGA-II).

19. The method of claim 1, wherein the machine learning algorithm is configured to perform the optimization by running a plurality of cycles across a plurality of different run configurations.

20. The method of claim 19, wherein a stopping criteria of at least about 0.001 mg/ml is applied to the plurality of cycles.

21. The method of claim 1, wherein the machine learning algorithm performs the optimization based at least on one or more parameters including number of generations, generation size, mutation rate, crossover probability, or parents' portion to determine offspring.

22. The method of claim 6, wherein a median difference in titer between a predicted fermentation titer and an actual titer for a sample fermentation run is within 10%.

23. The method of claim 1, wherein the first model is used to generate one or more out-of-sample predictions on titers that extend beyond or outside of the one or more physical limitations or processes of the fermentation system.

24. The method of claim 1, wherein the one or more machine learning models are configured to automatically adapt for a plurality of different sized fermentation systems.

25. The method of claim 1, wherein the one or more machine learning models comprises a third model that is configured to predict OUR or CER as a target variable based on the given set of input features.

26. The method of claim 25, wherein the OUR ranges from 100 mmol/L/hour to 750 mmol/L/hour.

27. The method of claim 25, wherein the CER ranges from about 100 mmol/L/hour to about 850 mmol/L/hour.

28. The method of claim 25, wherein the given set of input features comprises a subset of features that are accorded relatively higher feature importance weights.

29. The method of claim 28, wherein the subset of features comprise runtime, glucose and methanol feed, growth, induction conditions, or dissolved oxygen (DO) growth.

30. The method of claim 1, wherein the one or more machine learning models are trained using a training dataset from a fermentation database.

31. The method of claim 30, wherein the training dataset comprises at least 50 different features.

32. The method of claim 30, wherein the training dataset comprises at least 5000 data points.

33. The method of claim 30, wherein the one or more machine learning models are evaluated or validated based at least on a mean absolute error score using a hidden test set from the fermentation database.

34. The method of claim 1, wherein the one or more end process targets relate to cell viability.

35. The method of claim 1, wherein the more actual end process targets comprise an operational cost and/or a cycle time for running the fermentation system.

36. A method for fermentation process optimization, comprising: monitoring or tracking one or more actual end process targets of a fermentation system;

identifying one or more deviations over time by comparing the one or more actual end process targets to one or more predicted end process targets, wherein the one or more predicted end process targets are predicted using one or more machine learning models that are useable in a first mode or a second mode, wherein the first mode comprises using a first model to generate a prediction on a given set of input features, and the second mode comprises using the first model and/or an anchor prediction to generate the prediction on the given set of input features and a second model to generate a drag prediction, wherein the drag prediction by the second model is used as a datapoint to reduce a prediction error of the primary prediction by the first model; and determining, based at least on the one or more deviations over time, adjustments to be made to one or more process conditions in the fermentation system for optimizing the one or more actual end process targets in one or more subsequent batch runs.

37. The method of claim 36, wherein the one or more process conditions comprise media, pH, duration of fermentation cycle, temperature, feed rate, filtration for one or more impurities, agitation or stirring rate, oxygen uptake, or carbon dioxide generation.

38. The method of claim 36, further comprising: continuously making the adjustments to the one or more process conditions for the one or more subsequent batch runs as the fermentation system is operating.

39. The method of claim 38, wherein the adjustments are dynamically made to the one or more process conditions in real-time.

40. The method of claim 36, wherein the one or more process conditions comprises a set of upstream process conditions in the fermentation system.

41. The method of claim 36, wherein the one or more process conditions comprises a set of downstream process conditions in the fermentation system.

42. The method of claim 36, wherein the one or more actual end process targets comprise measured end of fermentation titers, and the one or more predicted end process targets comprise predicted end of fermentation titers that are predicted using the one or more machine learning models.

43. The method of claim 42, wherein optimizing the one or more actual end process targets comprise maximizing the measured end of fermentation titers for the one or more subsequent batch runs.

44. The method of claim 36, wherein the first and second models are different.

45. The method of claim 44, wherein the first and second models are intended to be used in a complementary manner to each other such that inherent characteristics in decision boundaries in the first and second models are accounted for.

46. The method of claim 36, wherein the first and second models are used as derivative free function approximations of a fermentation process in the fermentation system.

47. The method of claim 36, wherein the first model is a decision tree-based model.

48. The method of claim 36, wherein the first model comprises an adaptive boosting (AdaBoost) model.

49. The method of claim 36, wherein the second model comprises a neural network.

50. The method of claim 36, wherein the second model comprises an evolutionary algorithm.

51. The method of claim 36, wherein the one or more predicted end process targets are optimized by a machine learning algorithm.

52. The method of claim 51, wherein the machine learning algorithm that is used for the optimization is different from at least one of the machine learning models that are used to generate the prediction(s).

53. The method of claim 51, wherein the machine learning algorithm comprises a genetic algorithm.

54. The method of claim 53, wherein the genetic algorithm comprises a Non-dominated Sorting Genetic Algorithm (NSGA-II).

55. The method of claim 34, wherein the set of conditions is used to maximize the cell viability.

56. The method of claim 55, wherein the one or more actual end process targets comprise measured cell viability, and the one or more predicted end process targets comprise predicted cell viability that are predicted using the one or more machine learning models.

57. The method of claim 56, wherein optimizing the one or more actual end process targets comprise maximizing the measured cell viability for the one or more subsequent batch runs.

58. The method of claim 56, wherein optimizing the one or more actual end process targets comprises making the adjustments to the one or more process conditions, to ensure that a number of cells per volume of media for the one or more subsequent batch runs does not fall below a predefined threshold.

* * * * *